United States Patent
Cox

(10) Patent No.: US 9,622,753 B2
(45) Date of Patent: Apr. 18, 2017

(54) ANEURYSM TREATMENT DEVICE AND METHOD OF USE

(71) Applicant: MicroVention, Inc., Tustin, CA (US)

(72) Inventor: Brian J. Cox, Laguna Niguel, CA (US)

(73) Assignee: MicroVention, Inc., Tustin, CA (US)

(*) Notice: Subject to any disclaimer, the term of this patent is extended or adjusted under 35 U.S.C. 154(b) by 204 days.

(21) Appl. No.: 14/497,231

(22) Filed: Sep. 25, 2014

(65) Prior Publication Data

US 2015/0142042 A1    May 21, 2015

Related U.S. Application Data

(63) Continuation of application No. 13/557,068, filed on Jul. 24, 2012, now Pat. No. 8,870,909, which is a
(Continued)

(51) Int. Cl.
A61B 17/12    (2006.01)
A61F 2/86    (2013.01)
(Continued)

(52) U.S. Cl.
CPC .... *A61B 17/12113* (2013.01); *A61B 17/1219* (2013.01); *A61B 17/12022* (2013.01); *A61B 17/12118* (2013.01); *A61B 17/12172* (2013.01); *A61B 17/12186* (2013.01); *A61F 2/88* (2013.01); *A61F 2/90* (2013.01);
(Continued)

(58) Field of Classification Search
CPC ........ A61B 17/12022; A61B 17/12099; A61B 17/12109; A61B 17/12113; A61B 17/12118; A61B 17/1214; A61B 17/12145; A61B 17/1215; A61B 17/12168; A61B 17/12172; A61B 17/12177;
(Continued)

(56) References Cited

U.S. PATENT DOCUMENTS 3,868,956 A    3/1975    Alfidi et al.
4,512,338 A    4/1985    Balko et al.
(Continued)

FOREIGN PATENT DOCUMENTS

EP    0272760 A1    6/1988
EP    0518704 A1    12/1992
(Continued)

OTHER PUBLICATIONS

WIPO, U.S. International Search Authority, International Search Report and Written Opinion mailed Jul. 30, 2007 in International Patent Application No. PCT/US2005/001621, 11 pages.
(Continued)

*Primary Examiner* — Ryan J Severson
(74) *Attorney, Agent, or Firm* — Inskeep IP Group, Inc.

(57) ABSTRACT

The present application discloses an apparatus for treating vascular aneurysms and includes a radially expandable substantially cylindrical structure formed from a plurality of support members and defining a plurality of openings, and at least one reactive material strand selectively integrated into the substantially cylindrical structure. The reactive material is configured to assume a non-reacted state and a reacted state. The reactive material in the reacted state is configured to restrict a flow of blood to an aneurysm.

23 Claims, 12 Drawing Sheets

Related U.S. Application Data continuation of application No. 10/763,975, filed on Jan. 22, 2004, now Pat. No. 8,252,040, which is a continuation-in-part of application No. 09/909,715, filed on Jul. 20, 2001, now Pat. No. 7,572,288.

(51) Int. Cl.

| | | |
|---|---|---|
| *A61F 2/88* | (2006.01) | |
| *A61F 2/90* | (2013.01) | |
| *A61F 2/91* | (2013.01) | |
| *A61L 31/14* | (2006.01) | |
| *A61L 31/16* | (2006.01) | |
| *B65H 54/00* | (2006.01) | |
| *A61B 17/00* | (2006.01) | |
| *A61F 2/856* | (2013.01) | |
| *A61F 2/06* | (2013.01) | |
| *A61F 2/82* | (2013.01) | |

(52) U.S. Cl.
CPC .............. *A61F 2/91* (2013.01); *A61L 31/145* (2013.01); *A61L 31/16* (2013.01); *B65H 54/00* (2013.01); *A61B 2017/00526* (2013.01); *A61B 2017/00867* (2013.01); *A61B 2017/00898* (2013.01); *A61B 2017/1205* (2013.01); *A61F 2/856* (2013.01); *A61F 2002/065* (2013.01); *A61F 2002/823* (2013.01); *A61F 2230/0054* (2013.01); *A61L 2300/414* (2013.01); *A61L 2300/416* (2013.01); *A61L 2300/418* (2013.01)

(58) Field of Classification Search
CPC ...... A61B 17/1219; A61B 2017/00526; A61B 2017/00898; A61F 2002/823; A61L 31/145
See application file for complete search history.

(56) References Cited

U.S. PATENT DOCUMENTS

| | | |
|---|---|---|
| 4,553,545 A | 11/1985 | Maass et al. |
| 4,629,458 A | 12/1986 | Pinchuk |
| 4,655,771 A | 4/1987 | Wallsten |
| 4,655,918 A | 4/1987 | Eertink |
| 4,670,286 A | 6/1987 | Nyilas et al. |
| 4,718,907 A | 1/1988 | Karwoski et al. |
| 4,733,665 A | 3/1988 | Palmaz |
| 4,768,507 A | 9/1988 | Fischell et al. |
| 4,795,458 A | 1/1989 | Regan |
| 4,798,606 A | 1/1989 | Pinchuk |
| 4,800,882 A | 1/1989 | Gianturco |
| 4,813,925 A | 3/1989 | Anderson, Jr. et al. |
| 4,820,298 A | 4/1989 | Leveen et al. |
| 4,856,516 A | 8/1989 | Hillstead |
| 4,932,419 A | 6/1990 | de Toledo |
| 4,941,870 A | 7/1990 | Okada et al. |
| 4,950,258 A | 8/1990 | Kawai et al. |
| 4,954,126 A | 9/1990 | Wallstén |
| 4,990,155 A | 2/1991 | Wilkoff |
| 4,994,069 A | 2/1991 | Ritchart et al. |
| 5,015,253 A | 5/1991 | MacGregor |
| 5,019,090 A | 5/1991 | Pinchuk |
| 5,035,706 A | 7/1991 | Giantureo et al. |
| 5,037,391 A | 8/1991 | Hammerslag et al. |
| 5,041,126 A | 8/1991 | Gianturco |
| 5,061,275 A | 10/1991 | Wallstén et al. |
| 5,071,407 A | 12/1991 | Termin et al. |
| 5,108,417 A | 4/1992 | Sawyer |
| 5,116,365 A | 5/1992 | Hillstead |
| 5,122,136 A | 6/1992 | Guglielmi et al. |
| 5,133,732 A | 7/1992 | Wiktor |
| 5,135,536 A | 8/1992 | Hillstead |
| 5,141,502 A | 8/1992 | Macaluso, Jr. |
| 5,146,355 A | 9/1992 | Prince et al. |
| 5,147,370 A | 9/1992 | McNamara et al. |
| 5,151,105 A | 9/1992 | Kwan-Gett |
| 5,162,430 A | 11/1992 | Rhee et al. |
| 5,163,952 A | 11/1992 | Froix |
| 5,171,262 A | 12/1992 | MacGregor |
| 5,176,625 A | 1/1993 | Brisson |
| 5,183,085 A | 2/1993 | Timmermans |
| 5,192,297 A | 3/1993 | Hull |
| 5,197,978 A | 3/1993 | Hess |
| 5,217,484 A | 6/1993 | Marks |
| 5,222,969 A | 6/1993 | Gillis |
| 5,226,911 A | 7/1993 | Chee et al. |
| 5,234,437 A | 8/1993 | Sepetka |
| 5,234,456 A | 8/1993 | Silvestrini |
| 5,250,071 A | 10/1993 | Palermo |
| 5,256,146 A | 10/1993 | Ensminger et al. |
| 5,258,042 A | 11/1993 | Mehta |
| 5,261,916 A | 11/1993 | Engelson |
| 5,263,964 A | 11/1993 | Purdy |
| 5,304,195 A | 4/1994 | Twyford, Jr. et al. |
| 5,304,200 A | 4/1994 | Spaulding |
| 5,312,415 A | 5/1994 | Palermo |
| 5,314,444 A | 5/1994 | Gianturco |
| 5,314,472 A | 5/1994 | Fontaine |
| 5,342,300 A | 8/1994 | Stefanadis et al. |
| 5,342,387 A | 8/1994 | Summers |
| 5,350,397 A | 9/1994 | Palermo et al. |
| 5,354,295 A | 10/1994 | Guglielmi et al. |
| 5,383,887 A | 1/1995 | Nadal |
| 5,389,106 A | 2/1995 | Tower |
| 5,395,390 A | 3/1995 | Simon et al. |
| 5,405,377 A | 4/1995 | Cragg |
| 5,410,016 A | 4/1995 | Hubbell et al. |
| 5,415,664 A | 5/1995 | Pinchuk |
| 5,417,708 A | 5/1995 | Hall et al. |
| D359,802 S | 6/1995 | Fontaine |
| 5,433,723 A | 7/1995 | Lindenberg et al. |
| 5,441,516 A | 8/1995 | Wang et al. |
| 5,464,449 A | 11/1995 | Ryan et al. |
| 5,476,505 A | 12/1995 | Limon |
| 5,480,423 A | 1/1996 | Ravenscroft et al. |
| 5,484,449 A | 1/1996 | Amundson et al. |
| 5,500,013 A | 3/1996 | Buscemi et al. |
| 5,514,176 A | 5/1996 | Bosley, Jr. |
| 5,514,379 A | 5/1996 | Weissleder et al. |
| 5,514,380 A | 5/1996 | Song et al. |
| 5,522,822 A | 6/1996 | Phelps et al. |
| 5,522,836 A | 6/1996 | Palermo |
| 5,523,092 A | 6/1996 | Hanson et al. |
| 5,536,274 A | 7/1996 | Neuss |
| 5,540,701 A | 7/1996 | Sharkey et al. |
| 5,540,713 A | 7/1996 | Schnepp-Pesch et al. |
| 5,562,641 A | 10/1996 | Flomenblit et al. |
| 5,578,074 A | 11/1996 | Mirigian |
| 5,582,619 A | 12/1996 | Ken |
| 5,591,599 A | 1/1997 | Chang et al. |
| 5,601,593 A | 2/1997 | Freitag |
| 5,601,600 A | 2/1997 | Ton |
| 5,603,694 A | 2/1997 | Brown et al. |
| 5,607,445 A | 3/1997 | Summers |
| 5,609,627 A | 3/1997 | Goicoechea et al. |
| 5,609,628 A | 3/1997 | Keranen |
| 5,609,629 A | 3/1997 | Fearnot et al. |
| 5,613,981 A | 3/1997 | Boyle et al. |
| 5,630,829 A | 5/1997 | Lauterjung |
| 5,639,277 A | 6/1997 | Mariant et al. |
| 5,662,621 A | 9/1997 | Lafontaine |
| 5,674,241 A | 10/1997 | Bley et al. |
| 5,674,276 A | 10/1997 | Andersen et al. |
| 5,674,277 A | 10/1997 | Freitag |
| 5,674,295 A | 10/1997 | Ray et al. |
| 5,676,697 A | 10/1997 | McDonald |
| 5,690,667 A | 11/1997 | Gia |
| 5,690,671 A | 11/1997 | McGurk et al. |
| 5,693,085 A | 12/1997 | Buirge et al. |
| 5,702,373 A | 12/1997 | Samson |
| 5,707,389 A | 1/1998 | Louw et al. |
| 5,713,907 A | 2/1998 | Hogendijk et al. |
| 5,716,410 A | 2/1998 | Wang et al. |

(56) References Cited

U.S. PATENT DOCUMENTS

| | | | |
|---|---|---|---|
| 5,725,534 A | 3/1998 | Rasmussen | |
| 5,733,294 A | 3/1998 | Forber et al. | |
| 5,741,325 A | 4/1998 | Chaikof et al. | |
| 5,749,894 A * | 5/1998 | Engelson | A61B 17/12222 128/898 |
| 5,749,918 A | 5/1998 | Hogendijk et al. | |
| 5,750,585 A | 5/1998 | Park et al. | |
| 5,759,161 A | 6/1998 | Ogawa et al. | |
| 5,766,160 A | 6/1998 | Samson et al. | |
| 5,769,882 A | 6/1998 | Fogarty et al. | |
| 5,785,965 A | 7/1998 | Pratt et al. | |
| 5,800,454 A | 9/1998 | Jacobsen et al. | |
| 5,814,062 A | 9/1998 | Sepetka et al. | |
| 5,823,198 A | 10/1998 | Jones et al. | |
| 5,824,053 A | 10/1998 | Khosravi et al. | |
| 5,824,059 A | 10/1998 | Wijay | |
| 5,830,229 A | 11/1998 | Konya et al. | |
| 5,843,089 A | 12/1998 | Sahatjian et al. | |
| 5,895,391 A | 4/1999 | Farnholtz | |
| 5,911,161 A | 6/1999 | Harris | |
| 5,911,717 A | 6/1999 | Jacobsen et al. | |
| 5,911,731 A | 6/1999 | Pham et al. | |
| 5,935,148 A | 8/1999 | Villar et al. | |
| 5,941,249 A | 8/1999 | Maynard | |
| 5,951,599 A | 9/1999 | McCrory | |
| 5,980,514 A | 11/1999 | Kupiecki et al. | |
| 5,980,550 A | 11/1999 | Eder et al. | |
| 5,980,554 A | 11/1999 | Lenker et al. | |
| 5,989,242 A | 11/1999 | Saadat et al. | |
| 5,990,237 A | 11/1999 | Bentley et al. | |
| 6,015,431 A | 1/2000 | Thornton et al. | |
| 6,036,720 A | 3/2000 | Abrams et al. | |
| 6,053,940 A | 4/2000 | Wijay | |
| 6,059,815 A | 5/2000 | Lee et al. | |
| 6,060,534 A | 5/2000 | Ronan et al. | |
| 6,063,070 A * | 5/2000 | Eder | A61B 17/12022 606/1 |
| 6,063,111 A | 5/2000 | Hieshima et al. | |
| 6,086,577 A * | 7/2000 | Ken | A61B 17/12022 606/1 |
| 6,093,199 A | 7/2000 | Brown et al. | |
| 6,113,629 A | 9/2000 | Ken | |
| 6,120,847 A | 9/2000 | Yang et al. | |
| 6,123,714 A | 9/2000 | Gia et al. | |
| 6,140,127 A | 10/2000 | Sprague | |
| 6,152,144 A | 11/2000 | Lesh et al. | |
| 6,165,193 A | 12/2000 | Greene, Jr. et al. | |
| 6,165,194 A | 12/2000 | Denardo | |
| 6,168,592 B1 | 1/2001 | Kupiecki et al. | |
| 6,168,615 B1 | 1/2001 | Ken et al. | |
| 6,176,240 B1 | 1/2001 | Nikolchev et al. | |
| 6,177,095 B1 | 1/2001 | Sawhney et al. | |
| 6,184,266 B1 | 2/2001 | Ronan et al. | |
| 6,187,370 B1 | 2/2001 | Dinh et al. | |
| 6,190,402 B1 | 2/2001 | Horton et al. | |
| 6,193,708 B1 | 2/2001 | Ken et al. | |
| 6,201,065 B1 | 3/2001 | Pathak et al. | |
| 6,221,099 B1 * | 4/2001 | Andersen | A61F 2/04 623/1.15 |
| 6,224,892 B1 | 5/2001 | Searle | |
| 6,231,596 B1 | 5/2001 | Collins | |
| 6,231,597 B1 | 5/2001 | Deem et al. | |
| 6,238,403 B1 | 5/2001 | Greene, Jr. et al. | |
| 6,261,305 B1 * | 7/2001 | Marotta | A61F 2/82 606/200 |
| 6,264,695 B1 | 7/2001 | Stoy | |
| 6,273,908 B1 * | 8/2001 | Ndondo-Lay | A61F 2/885 606/194 |
| 6,280,457 B1 | 8/2001 | Wallace et al. | |
| 6,288,829 B1 | 9/2001 | Kimura | |
| 6,309,367 B1 | 10/2001 | Boock | |
| 6,364,893 B1 | 4/2002 | Sahatjian et al. | |
| 6,383,174 B1 * | 5/2002 | Eder | A61B 17/12022 606/1 |
| 6,398,808 B1 | 6/2002 | Palasis | |
| 6,419,686 B1 | 7/2002 | McLeod et al. | |
| 6,470,115 B1 | 10/2002 | Yonedubo | |
| 6,551,303 B1 | 4/2003 | Van Tassel et al. | |
| 6,554,849 B1 | 4/2003 | Jones et al. | |
| 6,569,179 B2 | 5/2003 | Teoh et al. | |
| 6,569,190 B2 | 5/2003 | Whalen, II et al. | |
| 6,592,614 B2 | 7/2003 | Lenker et al. | |
| 6,596,296 B1 | 7/2003 | Nelson et al. | |
| 6,605,111 B2 | 8/2003 | Bose et al. | |
| 6,605,294 B2 | 8/2003 | Sawhney | |
| 6,613,073 B1 | 9/2003 | White et al. | |
| 6,613,074 B1 | 9/2003 | Mitelberg et al. | |
| 6,663,607 B2 | 12/2003 | Slaikeu et al. | |
| 6,716,445 B2 * | 4/2004 | Won | A61K 9/205 424/426 |
| 6,723,108 B1 * | 4/2004 | Jones | A61B 17/12022 606/151 |
| 6,786,876 B2 | 9/2004 | Cox | |
| 6,811,560 B2 | 11/2004 | Jones et al. | |
| 6,878,384 B2 * | 4/2005 | Cruise | A61K 9/0024 424/423 |
| 6,953,468 B2 | 10/2005 | Jones et al. | |
| 6,953,473 B2 | 10/2005 | Porter | |
| 7,037,332 B2 | 5/2006 | Kutryk et al. | |
| 7,241,301 B2 * | 7/2007 | Thramann | A61B 17/12022 606/157 |
| 7,569,066 B2 * | 8/2009 | Gerberding | A61B 17/12022 606/200 |
| 7,572,288 B2 * | 8/2009 | Cox | A61B 17/12022 623/1.15 |
| 8,075,585 B2 * | 12/2011 | Lee | A61B 17/12022 606/200 |
| 8,252,040 B2 * | 8/2012 | Cox | A61B 17/12022 623/1.13 |
| 8,562,667 B2 * | 10/2013 | Cox | A61B 17/12022 623/1.15 |
| 8,715,312 B2 * | 5/2014 | Burke | A61B 17/12022 606/200 |
| 8,870,909 B2 * | 10/2014 | Cox | A61B 17/12022 606/200 |
| 2001/0000188 A1 | 4/2001 | Lenker et al. | |
| 2001/0000797 A1 | 5/2001 | Mazzocchi | A61B 17/0057 606/151 |
| 2001/0012961 A1 * | 8/2001 | Deem | A61B 17/12022 623/1.15 |
| 2001/0047202 A1 | 11/2001 | Slaikeu et al. | |
| 2002/0013618 A1 | 1/2002 | Marotta et al. | |
| 2002/0026228 A1 | 2/2002 | Schauerte | |
| 2002/0026232 A1 * | 2/2002 | Marotta | A61F 2/82 623/1.16 |
| 2002/0049495 A1 | 4/2002 | Kutryk et al. | |
| 2002/0052648 A1 | 5/2002 | McGuckin, Jr. et al. | |
| 2002/0123789 A1 | 9/2002 | Francis et al. | |
| 2002/0143349 A1 * | 10/2002 | Gifford, III | A61B 17/12022 606/157 |
| 2003/0004531 A1 | 1/2003 | Jones et al. | |
| 2003/0018294 A1 * | 1/2003 | Cox | A61B 17/12022 604/20 |
| 2003/0023190 A1 | 1/2003 | Cox | |
| 2003/0055451 A1 | 3/2003 | Jones et al. | |
| 2003/0120300 A1 | 6/2003 | Porter | |
| 2003/0135267 A1 * | 7/2003 | Solem | A61F 2/2451 623/1.18 |
| 2003/0139802 A1 | 7/2003 | Wulfman et al. | |
| 2003/0139806 A1 * | 7/2003 | Haverkost | A61F 2/06 623/1.33 |
| 2003/0171739 A1 | 9/2003 | Murphy et al. | |
| 2004/0034386 A1 * | 2/2004 | Fulton | A61B 17/12022 606/200 |
| 2004/0087998 A1 * | 5/2004 | Lee | A61B 17/12022 606/200 |
| 2004/0093076 A1 | 5/2004 | White et al. | |
| 2004/0098027 A1 * | 5/2004 | Teoh | A61B 17/12022 606/200 |
| 2004/0106945 A1 * | 6/2004 | Thramann | A61B 17/12022 606/200 |

(56) References Cited

U.S. PATENT DOCUMENTS

| | | | |
|---|---|---|---|
| 2004/0111112 A1 | 6/2004 | Hoffmann | |
| 2004/0172056 A1 | 9/2004 | Guterman et al. | |
| 2004/0186562 A1* | 9/2004 | Cox | A61B 17/12022 623/1.42 |
| 2004/0193206 A1* | 9/2004 | Gerberding | A61B 17/12022 606/200 |
| 2005/0033409 A1* | 2/2005 | Burke | A61B 17/12022 623/1.15 |
| 2009/0287297 A1* | 11/2009 | Cox | A61B 17/12022 623/1.22 |

FOREIGN PATENT DOCUMENTS

| | | |
|---|---|---|
| EP | 0627201 A1 | 12/1994 |
| EP | 1158332 A1 | 11/2001 |
| EP | 1220190 A2 | 7/2002 |
| EP | 1266631 A1 | 12/2002 |
| EP | 1271457 A2 | 2/2003 |
| WO | WO92/14408 A1 | 9/1992 |
| WO | WO94/16629 A1 | 8/1994 |
| WO | WO95/17859 A1 | 7/1995 |
| WO | WO9518585 A1 | 7/1995 |
| WO | WO97/42910 A1 | 11/1997 |
| WO | WO97/48351 A1 | 12/1997 |
| WO | WO98/50102 A1 | 11/1998 |
| WO | WO98/54930 A2 | 12/1998 |
| WO | WO99/02092 A1 | 1/1999 |
| WO | WO99/05977 A1 | 2/1999 |
| WO | WO99/40873 A1 | 8/1999 |
| WO | WO99/59479 A1 | 11/1999 |
| WO | WO99/62429 A1 | 12/1999 |
| WO | WO99/62432 A1 | 12/1999 |
| WO | WO99/65397 A1 | 12/1999 |
| WO | WO00/04845 A2 | 2/2000 |
| WO | WO00/07524 A1 | 2/2000 |
| WO | WO00/13593 A1 | 3/2000 |
| WO | WO00/18321 A1 | 4/2000 |
| WO | WO00/32112 A1 | 6/2000 |
| WO | WO00/44306 A1 | 8/2000 |
| WO | WO00/56247 A1 | 9/2000 |
| WO | WO00/57818 A1 | 10/2000 |
| WO | WO00/62711 A1 | 10/2000 |
| WO | WO00/74577 A1 | 12/2000 |
| WO | WO01/01890 A1 | 1/2001 |
| WO | WO01/03607 A2 | 1/2001 |
| WO | WO01/37892 A1 | 5/2001 |
| WO | WO01/41676 A1 | 6/2001 |
| WO | WO01/93780 A2 | 12/2001 |
| WO | WO02/05731 A1 | 1/2002 |
| WO | WO02/080782 A1 | 10/2002 |
| WO | WO02/087472 A1 | 11/2002 |
| WO | WO03/007823 A1 | 1/2003 |
| WO | WO03/071347 A1 | 8/2003 |
| WO | WO03/077984 A1 | 9/2003 |
| WO | WO2005/072196 A2 | 8/2005 |

OTHER PUBLICATIONS

WIPO, U.S. International Search Authority, International Search Report and Written Opinion mailed Feb. 14, 2006 in International Patent Application No. PCT/US2004/009528, 7 pages.

Lownie, S.P. et al., "Endovascular Therapy of a Large Vertebral Artery Aneurysm using Stent and Coils," *Canadian Journal of Neurological Sciences* vol. 2, No. 2, pp. 162-165, May 2000, 4 pages.

Klee, D. et al., "Bioactive Coating of Platinum Surfaces for Embolization Coils," *Society for Biomaterials* 2000, p. 215, 1 page.

Whitelock, J. et al., "Perecan coating of vascular grafts enhances endothelial cell growth," *Society for Biomaterials* 2000, p. 953, 1 page.

Raymond, J., M.D. et al., "Fibrinogen and Vascular Smooth Muscle Cell Grafts Promote Healing of Experimental Aneurysms Treated by Embolization," *Stroke* Aug. 1999;30(8):1657-64, 8 pages.

Kalra, G.S. et al., "Transcatheter Closure of Ventricular Septal Defect Using Detachable Steel Coil," *Heart* 82:395-396, 1999, 2 pages.

Wakhloo, A.K., M.D., Ph.D., et al., "Stents for Intracranial Aneurysms: The Beginning of a New Endovascular Era?", *Neurosurgery*, vol. 43, No. 2, pp. 377-379, Aug. 1998, 3 pages.

WIPO, U.S. International Search Authority, International Search Report mailed Nov. 6, 1997 in International Patent Application No. PCT/US1997/010882, 4 pages.

Viñuela, F., M.D. et al., "Guglielmi detachable coil embolization of acute intracranial aneurysm: perioperative anatomical and clinical outcome in 403 patients," *J Neurosurg*. 86:475-482, 1997, 9 pages.

Post, J.H., M.D. et al., "Experimental Nonsurgical Transcervical Sterilization with a Custom-Designed Platinum Microcoil," *Journal of Vascular and Interventional Radiology* vol. 8:113-118, Jan./Feb. 1997, 6 pages.

Massoud, T.F. et al., "Endovascular Treatment of Fusiform Aneurysms with Stents and Coils: Technical Feasibility in a Swine Model," *AJNR* 1:1953-1963, Nov. 1995, 11 pages.

Dawson, R.C. et al., "Treatment of Experimental Aneurysms Using Collagen-coated Microcoils," *Neurosurgery* 36:33-140, 1995, 8 pages.

Geremia, G. et al., "Embolization of Experimentally Created Aneurysms with Intravascular Stent Devices," *AJNR* 15:1223-1231, Aug. 1994, 10 pages.

Ahuja, A.A. et al., "Platinum Coil Coatings to Increase Thrombogenicity: A Preliminary Study in Rabbits," *AJNR* 14:794-788, Jul.-Aug. 1993, 5 pages.

Szikora, I. et al., "Combined Use of Stents and Coils to Treat Experimental Wide-Necked Carotid Aneurysms: Preliminary Results," *AJNR* 15:1091-1102, Jun. 1994, 11 pages.

Turjman, F. et al., "Combined Stent Implantation and Endosaccular Coil Placement for Treatment of Experimental Wide-Necked Aneurysms: A Feasibility Study in Swine," *AJNR* 15:1087-1990, Jun. 1994, 4 pages.

Schmitz-Rode, T. et al., "Self-expandable spindle for transcatheter vascular occlusion: in vivo experiments. Work in progress," abstract, *Radiology* Jul. 1993 ; 188(1):95-100, 1 page.

Park, K., Shalaby, W.S.W. and Park, H., *Biodegradable Hydrogels for Drug Delivery*, CRC Press, May 17, 1993, Chapter 3, "Types of Biodegradable Hydrogels," pp. 35-66, 31 pages.

Weber, J., M.D., "Techniques and results of therapeutic catheter embolization of congenital vascular defects," *Int. Angiol.* vol. 9:214-223, 1990, 10 pages.

\* cited by examiner

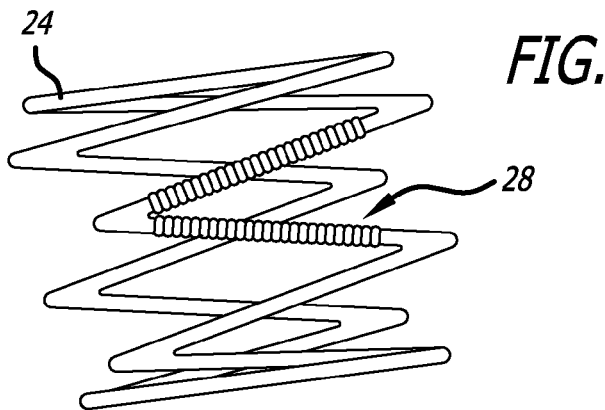
FIG. 5D
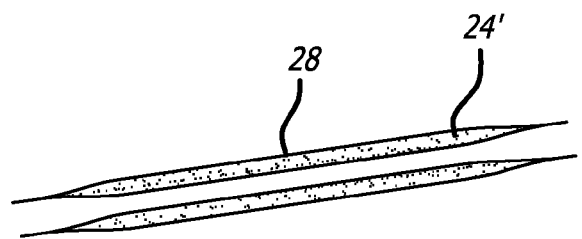
FIG. 5F
FIG. 5E
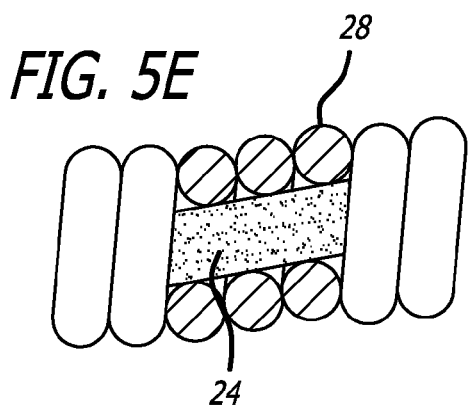
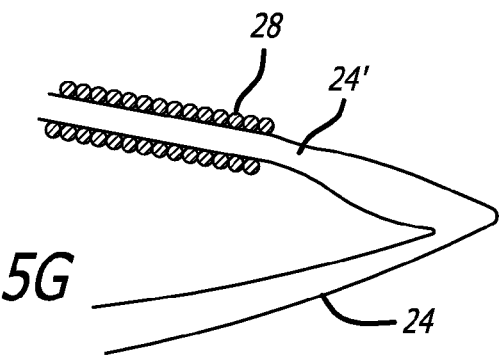
FIG. 5G

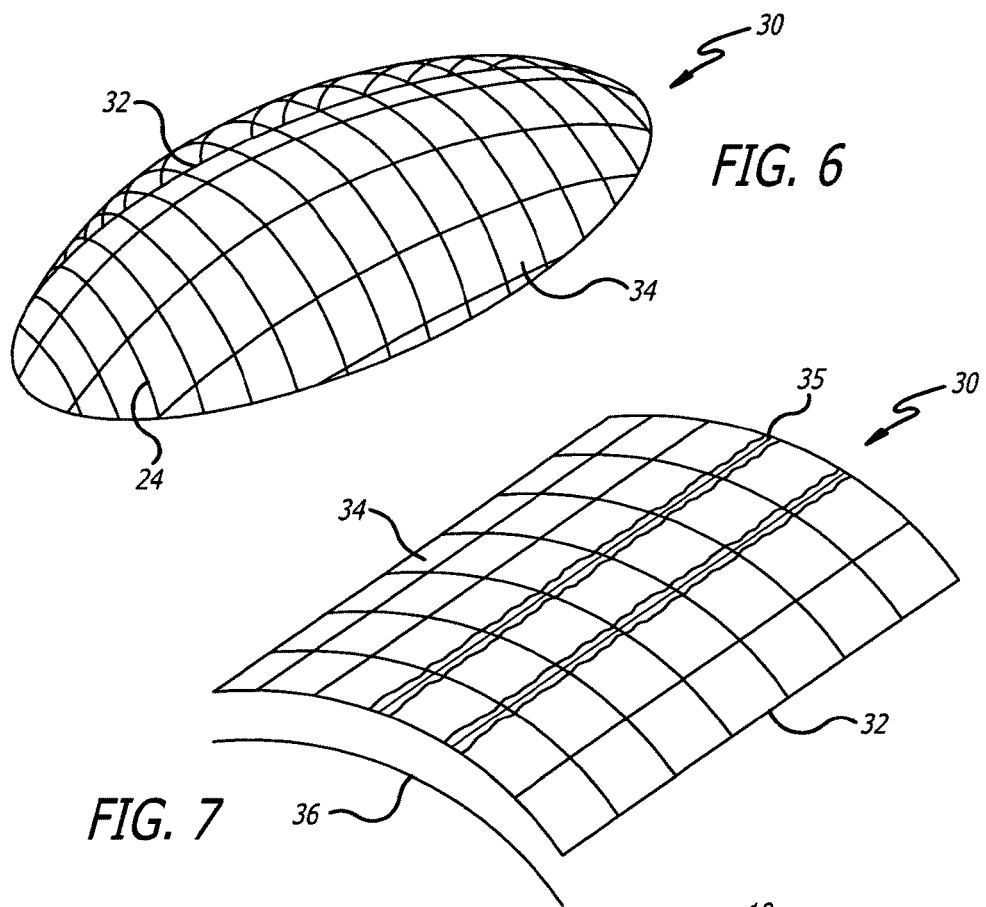
FIG. 6
FIG. 7
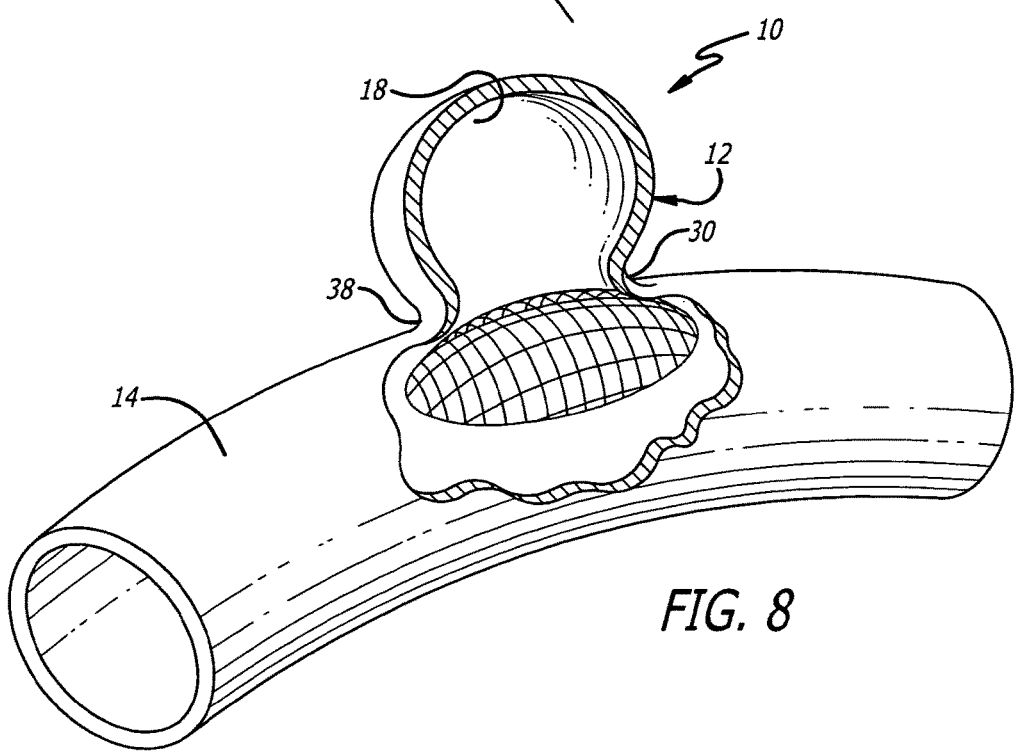
FIG. 8

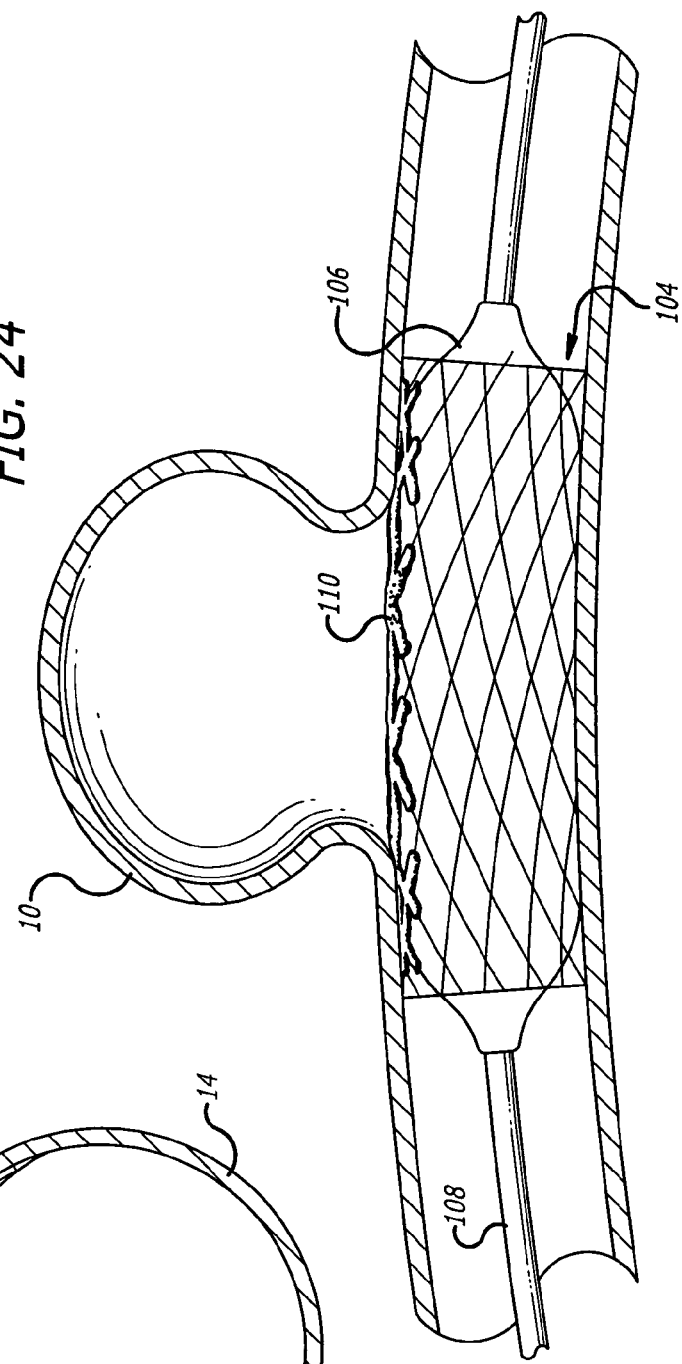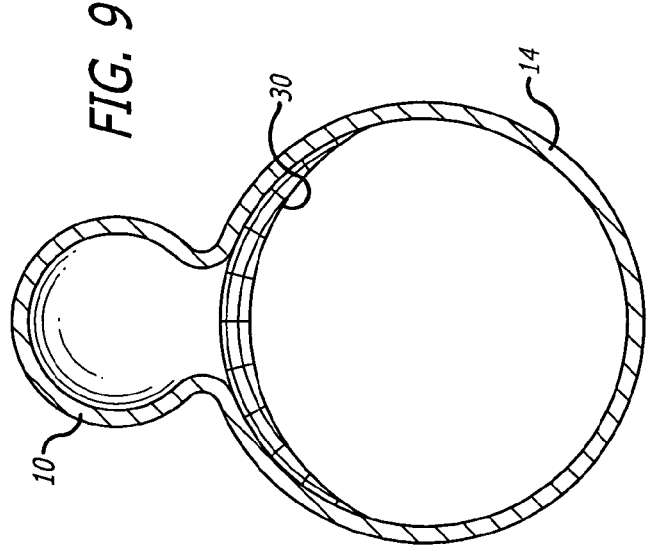

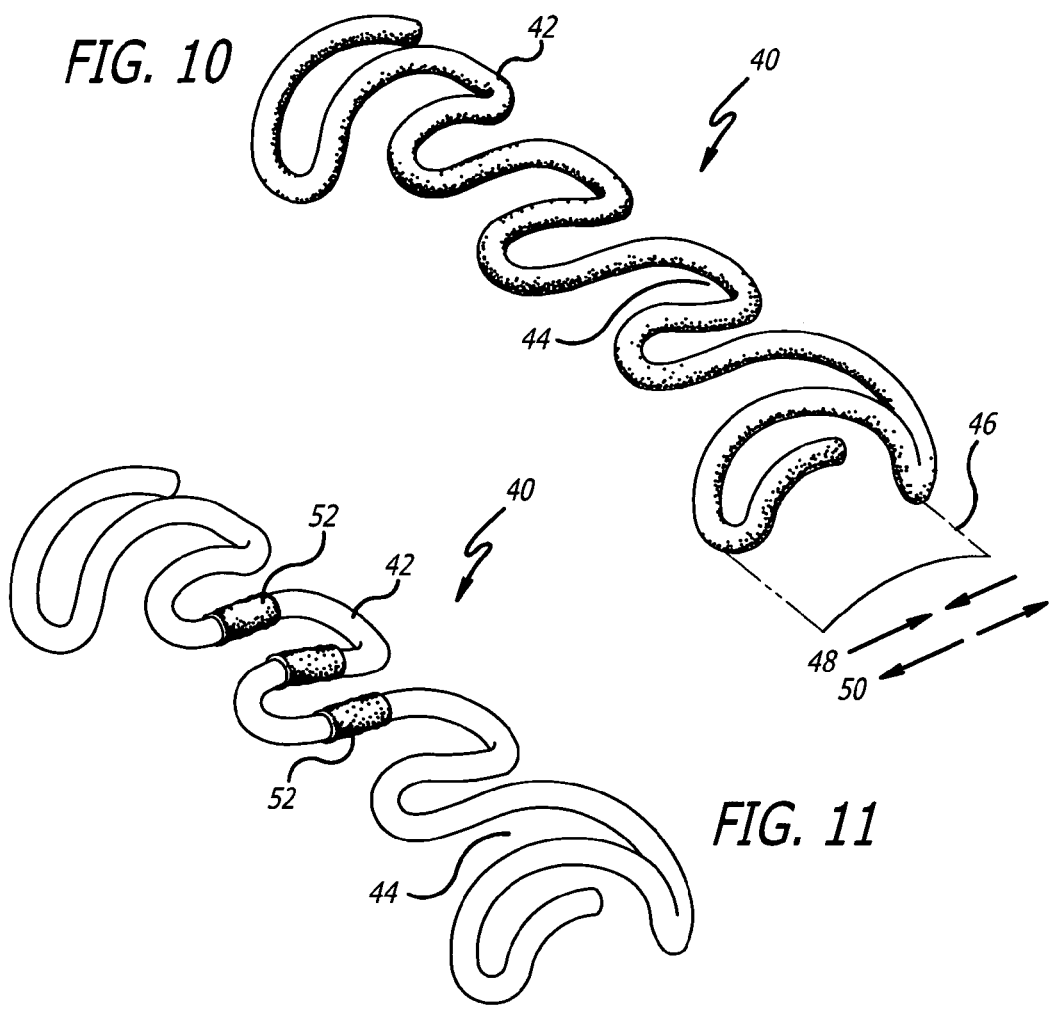
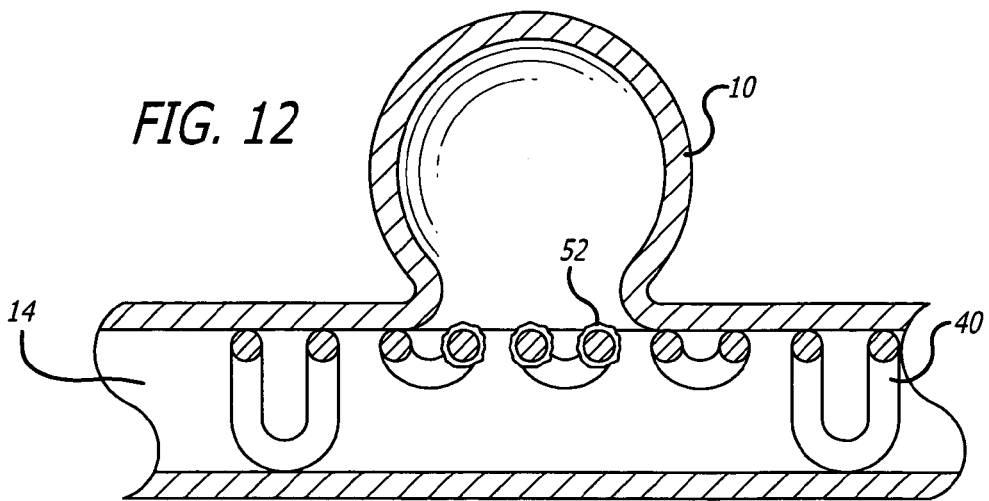

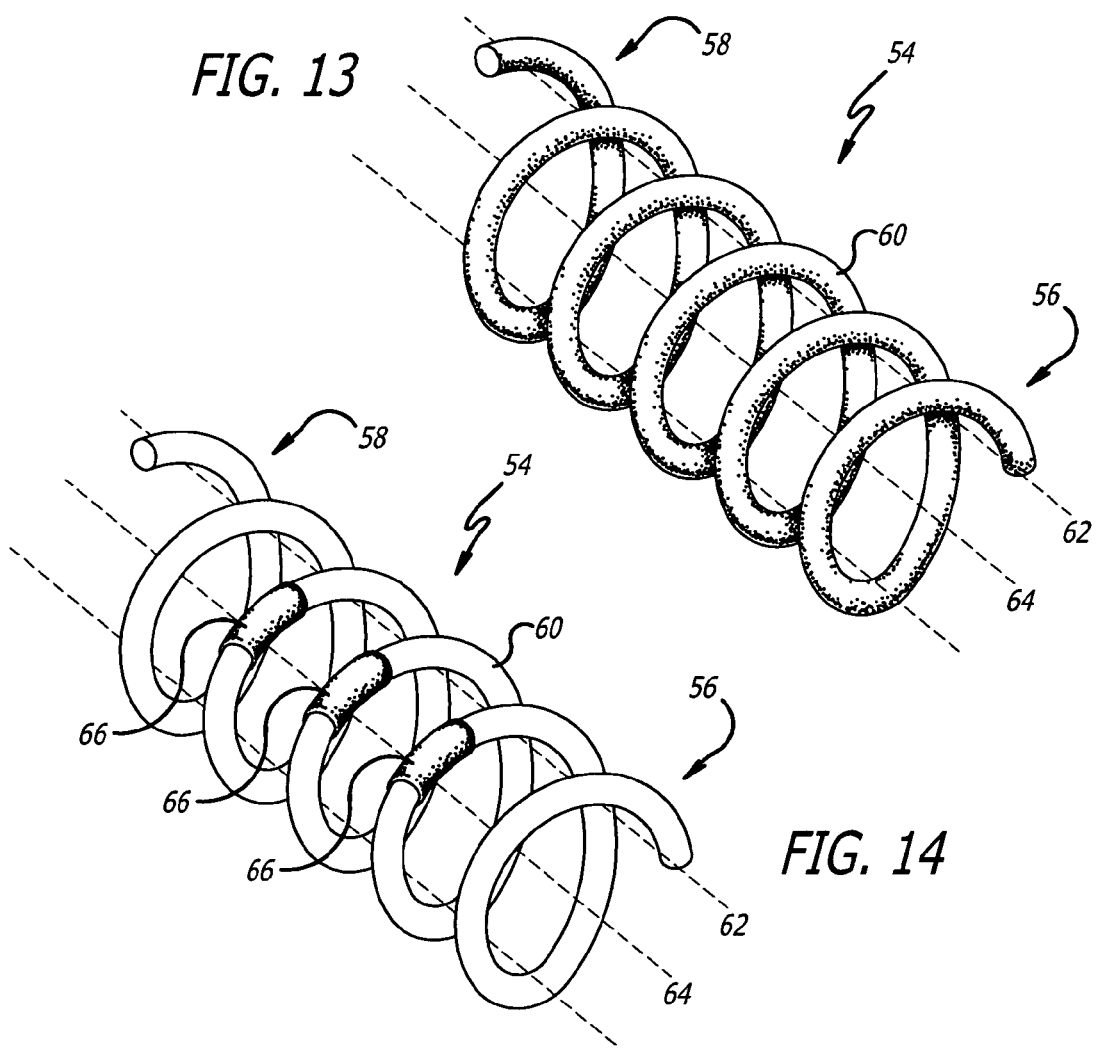
FIG. 13
FIG. 14
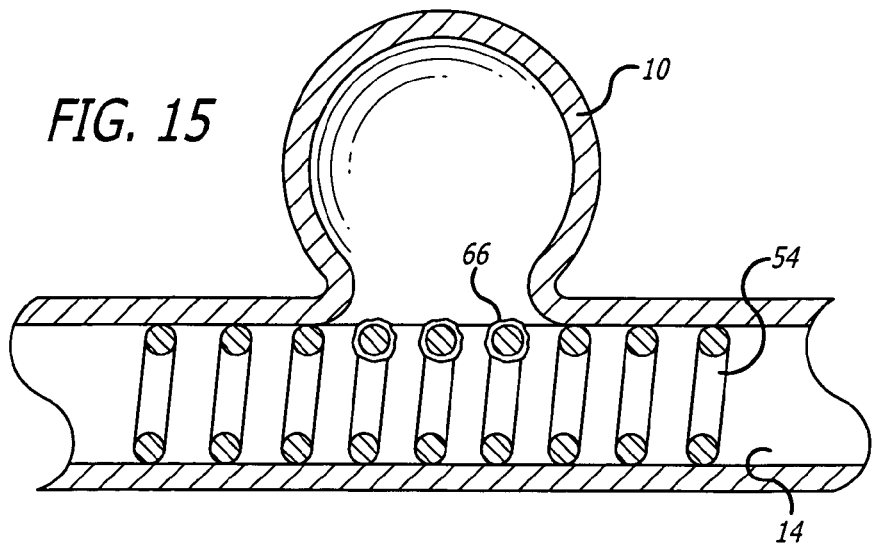
FIG. 15

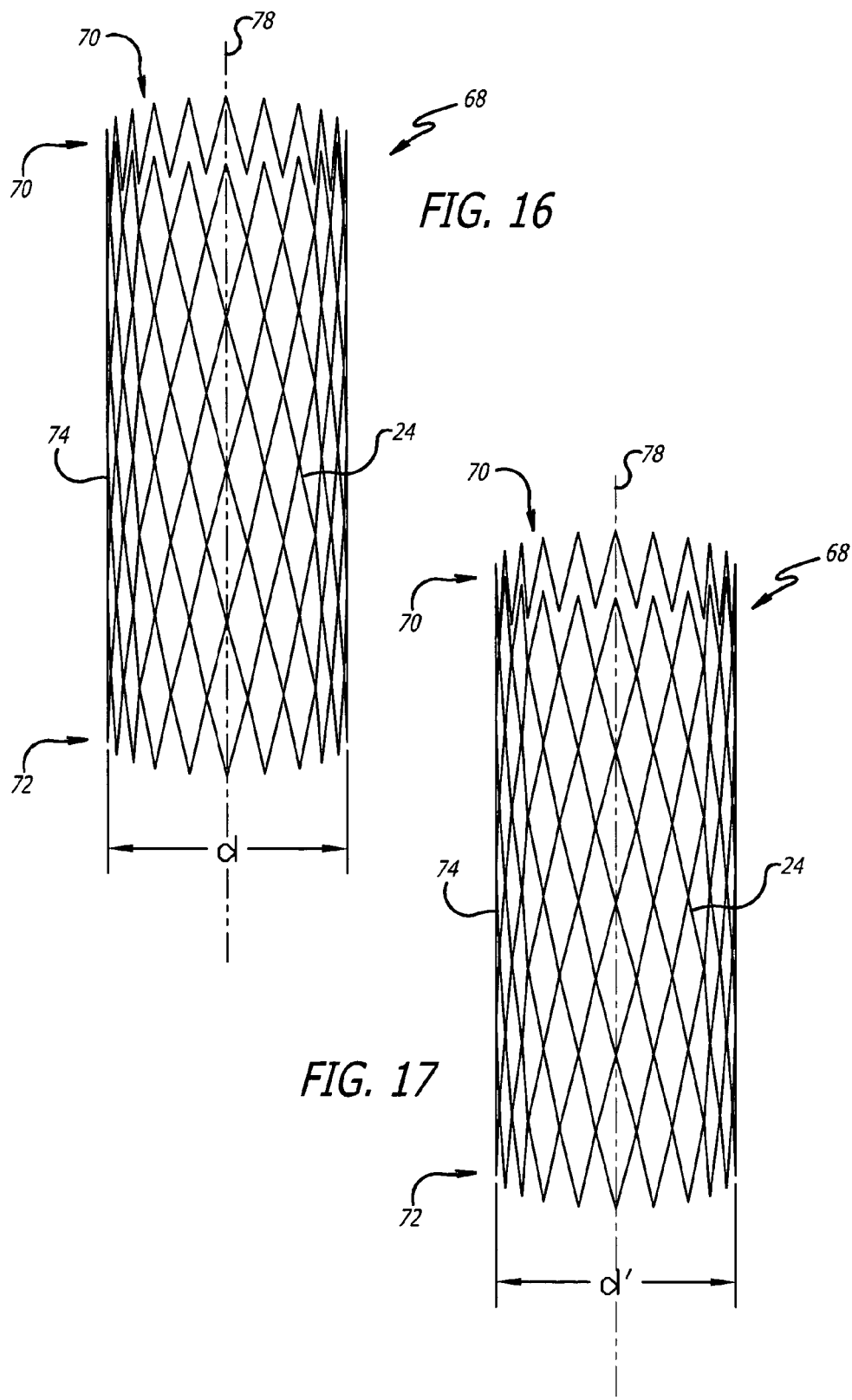

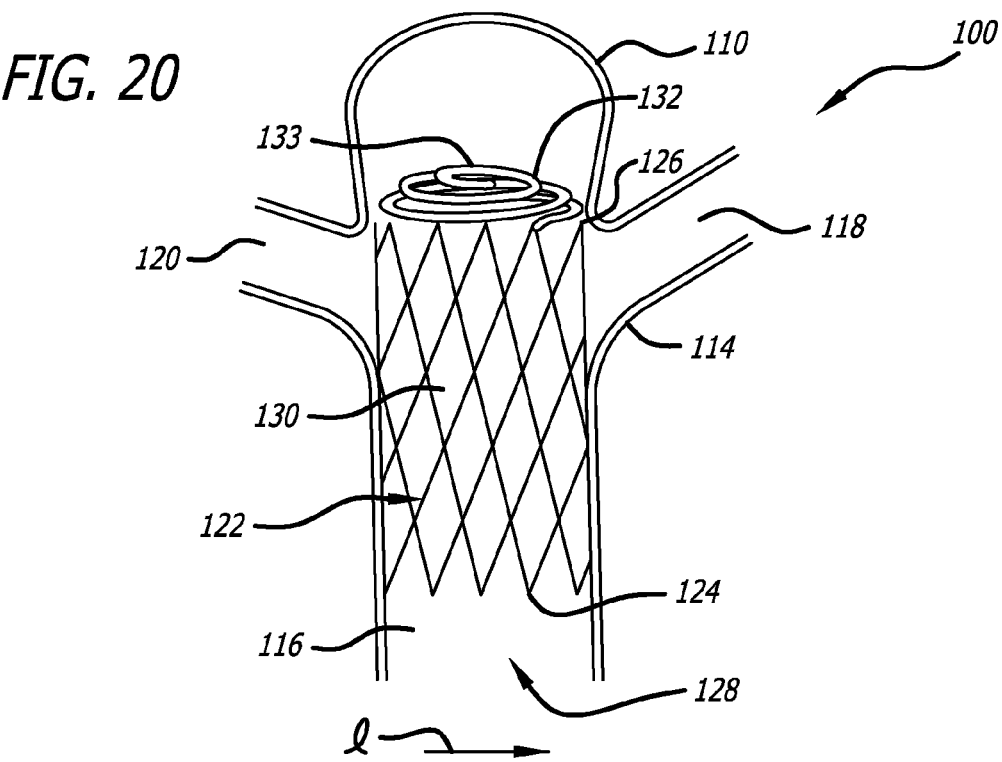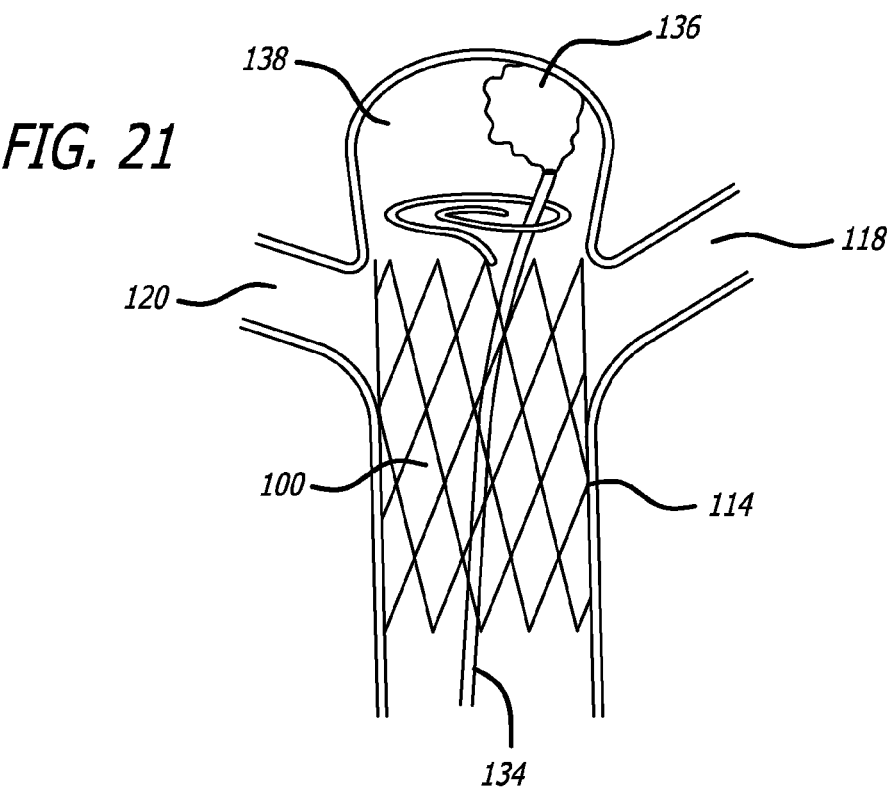

ANEURYSM TREATMENT DEVICE AND METHOD OF USE

CROSS REFERENCE TO RELATED APPLICATIONS

The present application is a continuation of U.S. patent application Ser. No. 13/557,068 filed Jul. 24, 2012 entitled Aneurysm Treatment Device And Method Of Use, which is a continuation of U.S. patent application Ser. No. 10/763,975 filed Jan. 22, 2004 entitled Aneurysm Treatment Device And Method Of Use, now U.S. Pat. No. 8,252,040 issued Aug. 28, 2012, which is a continuation-in-part of U.S. patent application Ser. No. 09/909,715 filed Jul. 20, 2001 entitled Aneurysm Closure Device And Method Of Use, now U.S. Pat. No. 7,572,288 issued Aug. 11, 2009, the contents of all of which are hereby incorporated by reference in their entireties. The entire contents of U.S. patent application Ser. No. 09/804,935, entitled Hydrogels That Undergo Volumetric Expansion In Response To Changes In Their Environment And Their Methods Of Manufacture And Use, filed on Mar. 31, 2001, naming Gregory M. Cruise and Michael J. Constant as co-inventors, now U.S. Pat. No. 6,878,384 issued Feb. 12, 2005, is hereby incorporated in its entirety by this reference.

BACKGROUND

Generally, the mammalian circulatory system is comprised of a heart, which acts as a pump, and a system of blood vessels which transport the blood to various points in the body. Due to the force exerted by the flowing blood on the blood vessel the blood vessels may develop a variety of vascular disabilities or dysfunctions. One common vascular dysfunction known as an aneurysm results from the abnormal widening of the blood vessel. Typically, vascular aneurysms are formed as a result of the weakening of the wall of a blood vessel and subsequent ballooning of the vessel wall. As shown in FIG. 1, the aneurysm 10 often comprises a narrow neck portion 12 which is in communication with the blood vessel 14 and a dome portion 16 in communication with the neck portion 12. As shown in FIG. 1 the neck portion 12 and the dome portion 16 form a cavity 18. Aneurysms have been known to form in a plurality of location though the body, including, for example, the brain, the abdomen, and throughout the circulatory system.

In response, several surgical techniques for treating aneurysms have been developed. Initially, an aneurysmectomy was required to repair the dysfunctional tissue. The aneurysmectomy procedure requires the surgeon to gain access to the aneurysm, excise the aneurysm, and replace the void with a prosthetic graft. Because this is a major surgical undertaking, the mortality rate of the procedure is relatively high. Commonly, the aneurysmectomy procedure is unavailable to patients with severe coronary or cerebral arteriosclerosis, severe restrictive pulmonary disease, and significant renal disease or other complicating factors. An alternate method of treating cerebral aneurysms called 'microsurgical clipping' requires the placement of a metallic clip across the neck of the aneurysm, thereby excluding the aneurysm from the blood flow.

In response to the shortcomings of the aneurysmectomy and the microsurgical clipping procedures, less invasive methods of treatment have been developed. Commonly, these procedures require the formation of an artificial vaso-occlusion, which is obtained by implanting a number of devices or suitable materials into the cavity 18 of the aneurysm, thereby resulting in a decrease in the flow of blood into the aneurysm. The reduced flow results in hemostasis and the formation of a clot. Generally, this procedure requires the surgeon to advance a micro-catheter to a location inside the aneurysm and deposit a biologically-compatible vaso-occlusive material or device therein. Typical vaso-occlusive devices and materials include platinum micro-coils, hog hair, microfibrillar collagen, various polymeric agents, material suspensions, and other space filling materials.

FIG. 2 shows an aneurysm 10 formed on a blood vessel 14, the aneurysm 10 having a vaso-occlusive device 20 positioned within the aneurysm dome 16. A disadvantage of filling an aneurysm with devices is that the vaso-occlusive mass may impinge on nerves or other biological structures, thereby resulting in adverse biological symptoms. For example, the impingement of the vaso-occlusive device 20 on structures or nerves within the brain, commonly known as 'mass effect', may result in adverse neurological symptoms. Another problem associated with vaso-occlusive devices is maintaining the device within the aneurysm. Blood flow through an otherwise functional blood vessel may be compromised should the device migrate from the aneurysm during or following implantation, thereby possibly resulting in a vascular embolism.

An alternate method of repairing an aneurysm has been developed which requires the implantation of a mechanical support device within the blood vessel near the neck portion of the aneurysm. Generally, these mechanical support devices, commonly referred to as "stents", comprise deployable mechanical support structures capable of delivery to a situs within the blood vessel through catheters. In addition to providing mechanical support to the dysfunctional vessel wall, the stent may include a mechanical structure which seeks to restrict the blood flow though the portion of the blood vessel proximate the aneurysm, thereby reducing or eliminating the aneurysm. Exemplary mechanical structures capable of restricting blood flow to an aneurysm include meshes or fenestrated structures which are positioned near an aneurysm 10 and restrict the flow of blood thereto.

FIG. 3 shows a stent 22 positioned in a blood vessel 14 proximal to an aneurysm 10. While a stent may provide adequate mechanical support to the blood vessel, these devices have demonstrated limited effectiveness in limiting blood flow to the aneurysm. As such, the aneurysm typically remains intact and may increase in size. In response, stents may be covered with various coatings designed to limit blood flow to the aneurysm. These coatings typically include biologically compatible polymers, films, and fabrics. However, the application of these coatings to the stents increases the cross-sectional diameter of the device, thereby resulting in a high profile stent-graft. As a result, the blood flow through the blood vessel is reduced by the presence of a high profile stent-graft. In addition, device profile is a significant problem for the treatment of cerebral aneurysms due to the small size of the cerebral blood vessels, therefore requiring the device to be deliverable to the aneurysm through a micro-catheter. As such, high profile stent-grafts are typically not used in the treatment of cerebral aneurysms.

Thus, there is presently an ongoing need for a device and method for effectively treating aneurysms without significantly affecting blood flow through the blood vessel.

SUMMARY

The aneurysm treatment devices of the present application effectively occlude or inhibit blood flow to an aneurysm without substantially impairing blood flow through the blood vessel. In addition, the aneurysm treatment devices of the present application are capable of being applied to a variety of aneurysms formed on blood vessels throughout the body.

In one embodiment, the aneurysm treatment device of the present invention comprises at least one support member and reactive material selectively applied to the support member. The at least one support member, which has at least a first surface capable of receiving the reactive material, provides a substrate for receiving the reactive material. Alternatively, the at least one support member may also provide support to weakened vascular tissue. The reactive material has a non-reacted state and a reacted state. In a reacted stated the reactive material, as selectively applied to the at least one support member, is capable of restricting or occluding the flow of blood to the aneurysm. In an alternate embodiment, the at least one support member may be manufactured from or otherwise incorporate reactive material therein. The device is preferably controllably released from an elongate delivery apparatus. The release mechanism may be any of the vaso-occlusive device and stent detachment means known in the art including but not limited to mechanical, electrolytic, electro-mechanical, thermal, hydraulic, and shape-memory means.

In an alternate embodiment, the present invention is directed to a vascular patch comprising a radially and axially flexible patch body formed by a plurality of interlocking support members. The interlocking support members, which are capable of supporting vascular tissue, form a plurality of fenestrations. A reactive material capable of restricting or occluding the flow of blood to an aneurysm is selectively applied to, woven into, integral to, or otherwise incorporated into the interlocking support member. For example, the interlocking member may be manufactured from fibrous or formed reactive material.

In yet another embodiment, the present invention is directed to a coiled bridge device comprising radially and axially flexible resilient sinusoidal body member which defines a plurality of openings. The sinusoidal body member has a first radius of curvature R and a second radius of curvature R', wherein R' is larger than R. The sinusoidal body member is formed by at least one support member and has a reactive material capable of restricting or occluding the flow of blood to an aneurysm, selectively applied thereto.

In another embodiment, the present invention is directed to a helical stent having a radially and axially flexible cylindrical body member positioned between a first end and a second end. The cylindrical body member, which is formed by at least one support member capable of supporting vascular tissue, defines an internal lumen which is in communication with the first and second ends. A reactive material capable of restricting or occluding the flow of blood to an aneurysm is selectively applied to the at least one support member.

In yet another embodiment, the present invention is directed to a helical stent having a radially and axially flexible cylindrical body member positioned between a first end and a second end. The cylindrical body member, which is formed by at least one support member capable of supporting vascular tissue, defines an internal lumen which is in communication with the first and second ends. A reactive material capable of restricting or occluding the flow of blood to an aneurysm is selectively applied to the at least one support member.

In another embodiment, the present invention is directed to a reticulated expandable stent comprising radially and axially flexible cylindrical body member positioned between a first end and a second end. The cylindrical body member, which is formed by at least one support member capable of supporting vascular tissue, defines an internal lumen which is in communication with the first and second ends. A reactive material capable of restricting or occluding the flow of blood to an aneurysm is selectively applied to the at least one support member.

In still another embodiment, the present invention is directed to a bifurcated vascular support device comprising a bifurcated body member positioned between a first end, a second end, and a third end. The bifurcated body member further defines an internal lumen which communicates with the first, second, and third ends. The bifurcated body member is formed by at least one support member capable of supporting vascular tissue. A reactive material capable of restricting or occluding the flow of blood to an aneurysm is selectively applied to the at least one support member.

In another embodiment, the present invention is directed to an intra-aneurysmal bridge device comprising a flexible bridge body in communication with at least two engagement members. The at least two engagement members cooperatively form a joint. A reactive material capable of restricting or occluding the flow of blood to an aneurysm is selectively applied to the at least two engagement members.

The present invention also discloses a novel method of treating a vascular aneurysm. More particularly, the novel method of treating vascular aneurysms comprises the steps of providing a device for treating vascular aneurysms having a reactive material applied thereto, delivering the device to a vascular aneurysm, supporting the tissue near the aneurysm with the device, and allowing the reactive material to react thereby permitting the flow of blood through the blood vessel while restricting or occluding the flow of blood to the aneurysm.

In yet another embodiment, the present application discloses an apparatus for treating vascular aneurysms and includes a radially expandable structure formed from at least one support member and defining a plurality of openings, and at least one reactive material selectively applied to a portion of the at least one support member. The reactive material is configured to assume a reacted state which restricts the flow of blood to an aneurysm.

In another embodiment, the present application discloses an apparatus for treating aneurysms and includes at least one support member defining an expandable support body, at least one reactive material selectively applied to at least one support member and having a non-reacted state and a reacted state. The support member has a diameter D in a non-reacted state and a diameter D' in a reacted state, wherein diameter D' is larger than diameter D.

In another embodiment, the present application is directed to an apparatus for treating vascular aneurysms and includes an occlusive support defined by one or more support members and having a first end and a second end and a lumen formed therein, one or more fenestrations formed on the occlusive support and configured to permit blood to flow therethrough, an end cap secured to the second end and configured to restrict the flow of blood therethrough.

The present application further discloses a method of treating a vascular aneurysm and includes providing a device having a reactive material selectively applied to at least one support member, delivering the device to a position in a blood vessel proximate a vascular aneurysm, expanding the device to approximately a diameter of a blood vessel, and activating the reactive material disposed on the device to reduce the flow of blood into the aneurysm.

In another embodiment, the present application discloses a method of treating a vascular aneurysm and includes providing a device having at least one support member and an end cap secured to the support member, delivering the device to a position in a blood vessel proximate a vascular aneurysm, expanding the device to approximately the diameter of the blood vessel, and reducing a flow of blood to the aneurysm with the end cap while permitting blood flow through the blood vessel.

In another embodiment, the present application discloses a method of treating a vascular aneurysm and includes providing a device having at least one support member and an end cap secured to the support member, delivering the device to a position in a blood vessel proximate a vascular aneurysm, expanding the device to approximately the diameter of the blood vessel, delivering a catheter through the blood vessel to a position proximate to the vascular aneurysm, inserting a space occupying material into the aneurysm, and maintaining the space occupying material within the aneurysm with the end cap to reduce the flow of blood into the aneurysm.

In another embodiment, the present application discloses a method of treating a vascular aneurysm and includes providing a device having at least one support member and an end cap secured to the support member, the end cap having a reactive material disposed thereon, delivering the device to a position in the blood vessel proximate a vascular aneurysm, expanding the device to approximately a diameter of a blood vessel, delivering a catheter through the blood vessel to a position proximate to the vascular aneurysm, inserting a space occupying material into the aneurysm, and activating the reactive material to maintain the space occupying material within the aneurysm with the end cap to reduce the flow of blood into the aneurysm.

Other objects and further features of the aneurysm treatment device of the present application will become apparent from the following detailed description when read in conjunction with the attached drawings.

BRIEF DESCRIPTION OF THE DRAWINGS

The aneurysm treatment device of the present application will be explained in more detail byway of the accompanying drawings, wherein:

FIG. 5d shows a perspective view of an embodiment of an aneurysm treatment device having a reactive material strand wrapped around a support member;

FIG. 5e shows a cross-sectional view of an embodiment of an aneurysm treatment device having a reactive material strand wrapped around a support member;

FIG. 5f shows a sectional view of an embodiment of an aneurysm treatment device having a support member with a variable tangential width and a reactive material strand applied thereto;

FIG. 5g shows another sectional view of an embodiment of an aneurysm treatment device having a support member with a variable tangential width and a reactive material strand applied thereto;

FIG. 6 shows a perspective view of an embodiment of an aneurysm treatment device comprising a vascular patch device useful in restricting the flow of blood to a vascular aneurysm;

FIG. 7 shows another perspective view of an embodiment of an aneurysm treatment device comprising a vascular patch device useful in restricting the flow of blood to a vascular aneurysm;

FIG. 8 shows a perspective view of an embodiment of an aneurysm treatment device positioned within a blood vessel proximate a vascular aneurysm;

FIG. 9 shows a cross-sectional view of an embodiment of an aneurysm treatment device positioned within a blood vessel proximate a vascular aneurysm;

FIG. 10 shows a perspective view of an embodiment of an aneurysm treatment device comprising a coiled bridge device useful in restricting the flow of blood to a vascular aneurysm;

FIG. 11 shows a perspective view of another embodiment of an aneurysm treatment device comprising a coiled bridge device useful in restricting the flow of blood to a vascular aneurysm;

FIG. 12 shows a cross-sectional view of an embodiment of the aneurysm treatment device of FIG. 11 positioned within a blood vessel proximate a vascular aneurysm;

FIG. 13 shows a perspective view of an embodiment of an aneurysm treatment device comprising a helical stent device useful in restricting the flow of blood to a vascular aneurysm;

FIG. 14 shows a perspective view of another embodiment of an aneurysm treatment device comprising a helical stent device useful in restricting the flow of blood to a vascular aneurysm;

FIG. 15 shows a cross-sectional view of the embodiment of the aneurysm treatment device shown in FIG. 14 positioned within a blood vessel proximate a vascular aneurysm;

FIG. 16 shows a perspective view of another embodiment of an aneurysm treatment device comprising a reticulated stent device useful in restricting the flow of blood to a vascular aneurysm;

FIG. 17 shows a perspective view of another embodiment of the reticulated stent device useful in restricting the flow of blood to a vascular aneurysm;

FIG. 20 shows a sectional view of an embodiment of an aneurysm treatment device comprising an occlusive support positioned within a blood vessel proximate to a vascular aneurysm;

FIG. 21 shows a sectional view of an embodiment of an aneurysm treatment device having a catheter delivering a space occupying material to a vascular aneurysm through an occlusive support positioned within the blood;

FIG. 24 shows a perspective view of an embodiment of an aneurysm treatment device positioned on an expandable balloon micro-catheter within a blood vessel.

DETAILED DESCRIPTION

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

The aneurysm treatment devices of the present application are generally used to restrict the ability of blood flowing through a blood vessel from entering an aneurysm formed thereon or to otherwise limit the amount of blood within an aneurysm. The devices disclosed herein may be applied to a blood vessel in a variety of ways, including, without limitation, conventional surgical techniques and minimally invasive surgical techniques utilizing catheters of various sizes, balloon catheters, micro-catheters, and other ways generally known in the art of minimally invasive surgery. The aneurysm treatment devices disclosed herein may be used to repair a variety of aneurysms at various locations throughout the body. For example, in one embodiment these devices may be used in procedures to repair or otherwise treat cerebrovascular aneurysms.

The devices and methods of the present application have particular compatibility with the materials and methods of manufacture and use disclosed in co-pending U.S. patent application Ser. No. 09/804,935 filed on Mar. 13, 2001, entitled "Hydrogels That Undergo Volumetric Expansion In Response To Changes In Their Environment And Their Methods Of Manufacture And Use," and co-pending U.S. patent application Ser. No. 09/909,715 filed on Jul. 20, 2001, entitled "Aneurysm Treatment Devices and Methods of Use," each of which has been assigned to the assignee of the present application and which are incorporated by reference as if set forth herein in their entirety. Those skilled in the art will appreciate that the present invention may be manufactured with one or more of a variety of alternate reactive materials applied thereto, including, for example, collagen-polymer conjugate materials, photopolymerizable biodegradable materials, and other biodegradable cross-linked hydrogels known in the art.

Figure 1:
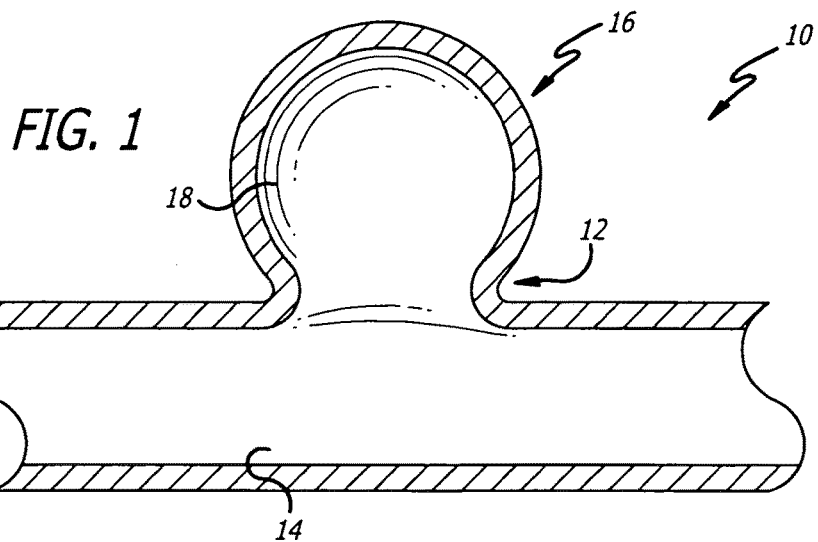
FIG. 1 shows a cross-sectional view of a blood vessel having a vascular aneurysm formed on its wall.

Aneurysms form as a result of outward pressure applied to a diseased or damaged blood vessel wall by blood flowing within the vessel, thereby resulting in a weakened section of tissue ballooning outwardly from a blood vessel. FIG. 1 shows an aneurysm 10 comprising a neck portion 12 in communication with a blood vessel 14 and having a dome portion 16 defining aneurysm cavity 18. Those skilled in the art will appreciate FIG. 1 illustrates an exemplary vascular aneurysm and is not intended to limit the scope or intent of the present invention.

Figure 2:
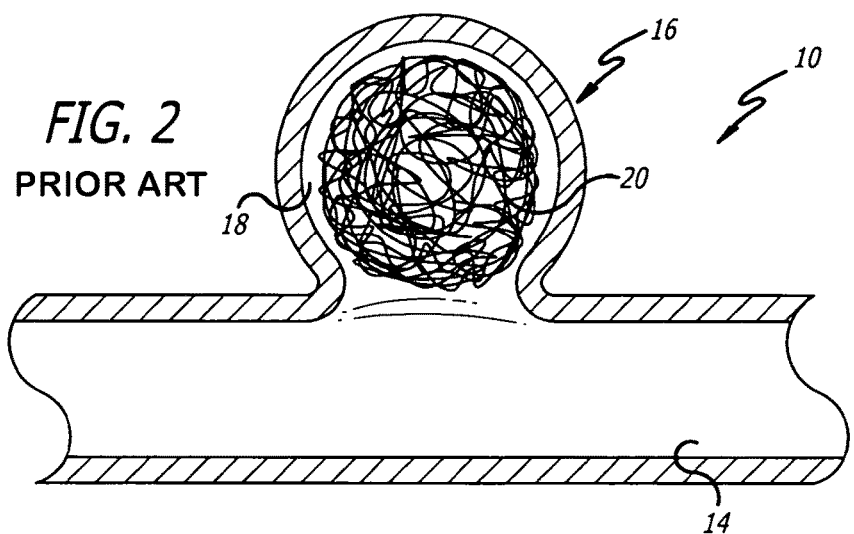
FIG. 2 shows a cross-sectional view of a prior art method of treating vascular aneurysm requiring the deposition of space-filling material within the vascular aneurysm.
Figure 3:
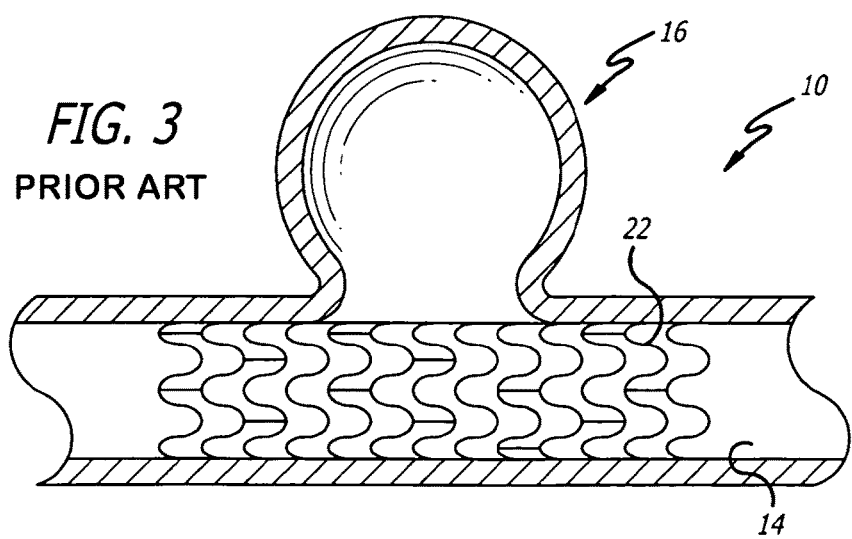
FIG. 3 shows a cross-sectional view of an alternate prior art method of treating vascular aneurysm wherein a mechanical stent is positioned near an aneurysm.

One method of treating an aneurysm requires the formation of an embolism proximate to or within the aneurysm, thereby restricting or depriving the aneurysm of blood flow and reducing the likelihood the aneurysm will rupture. FIGS. 2 and 3 show prior art devices used to repair aneurysms by artificially creating embolisms within or proximate to the aneurysm. In FIGS. 2 and 3 the reference numerals 10, 12, 14, 16, and 18 have analogous meanings to the reference numerals identifying the features of FIG. 1. FIG. 2 shows an aneurysm 10 in communication with a blood vessel 14. As shown, a vaso-occlusive device 20 is positioned within the aneurysm cavity 18. Typically, a micro-catheter or other device is used to inject or otherwise insert the vaso-occlusive device 20 into the aneurysm cavity 18, thereby decreasing the volume of the aneurysm capable of receiving blood from the blood vessel 14. FIG. 3 shows another device useful in treating aneurysms. As shown in FIG. 3, a stent 22 is positioned within a blood vessel 14 proximate to an aneurysm 10. A stent 22 is a mechanical scaffold used to provide support to otherwise incompetent or weakened tissue or to or maintain the patency of a narrowed or occluded blood vessel.

The present application discloses various embodiments of devices useful for the embolization or isolation of aneurysms. More particularly, the present application discloses various structures capable of implantation within an aneurysm or configured to be inserted into a blood vessel proximate to an aneurysm. Exemplary aneurysm treatment devices disclosed herein include, without limitation, neck bridges, vascular patches, stents, and intra-aneurysmal implants. In one embodiment, an aneurysm treatment device may include a series of interlocking or otherwise connected support members forming a predetermined shape. In an alternate embodiment, the aneurysm treatment device comprises an implant body which may be partially or completely inserted into an aneurysm formed on a blood vessel. The implant body may form a predetermined shape or, in the alternative, may form a random shape.

Figure 4:
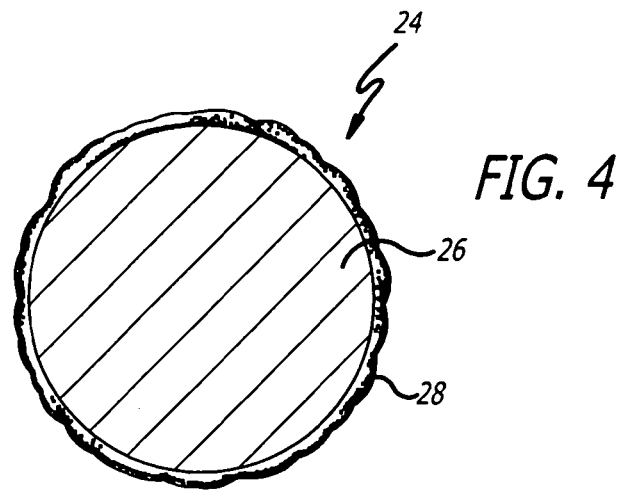
FIG. 4 shows a sectional view of a support member of an aneurysm treatment device having non-reacted reactive material disposed thereon.
Figure 5A:
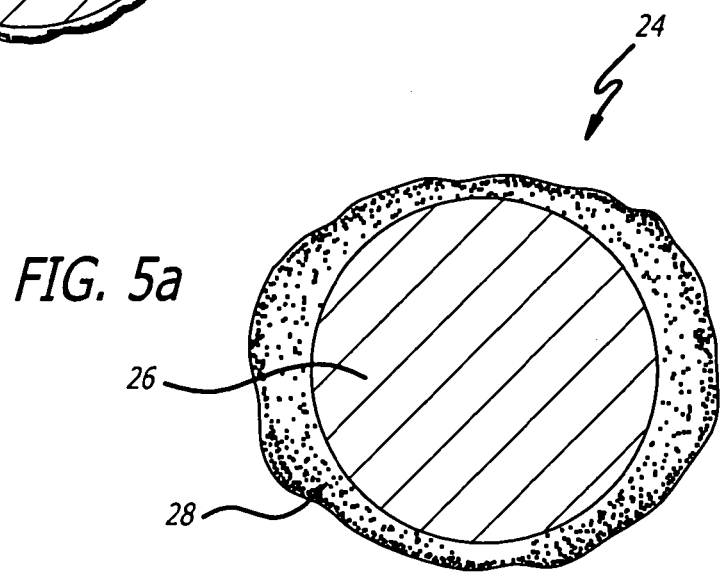
FIG. 5a shows a sectional view of a support member of an aneurysm treatment device having reacted reactive material disposed thereon.

FIGS. 4 and 5a show cross sectional views of a portion of a support member 24 as used in the formation of a number of embodiments of the aneurysm treatment device of the present application before and following implantation. As shown in FIG. 4, the support member 24 may comprise a device substrate 26 having a reactive coating or material 28 applied to the exterior portion thereof prior to implantation. The support member 24 having a non-reacted reactive coating thereon has a first diameter of D. FIG. 5a shows reactive coating 28 disposed on the support member 24 in a reacted state, wherein the reactive coating 28 has expanded outwardly from the device substrate 26 in a preferential direction. As shown, in a reacted state the support member 24 assumes a second diameter of D', wherein the second diameter D' is larger than the first diameter D. For example, in one embodiment the second diameter D' is about 20% larger than the first diameter D. In the illustrated embodiment, the reactive coating 28 has expanded more along the horizontal axis than the vertical axis. This permits the coating to inhibit flow outwardly through the device in the radial direction while minimizing its impact on longitudinal flow through the device and also minimizing the coating's impact on the overall profile of the device.

Figure 5B:
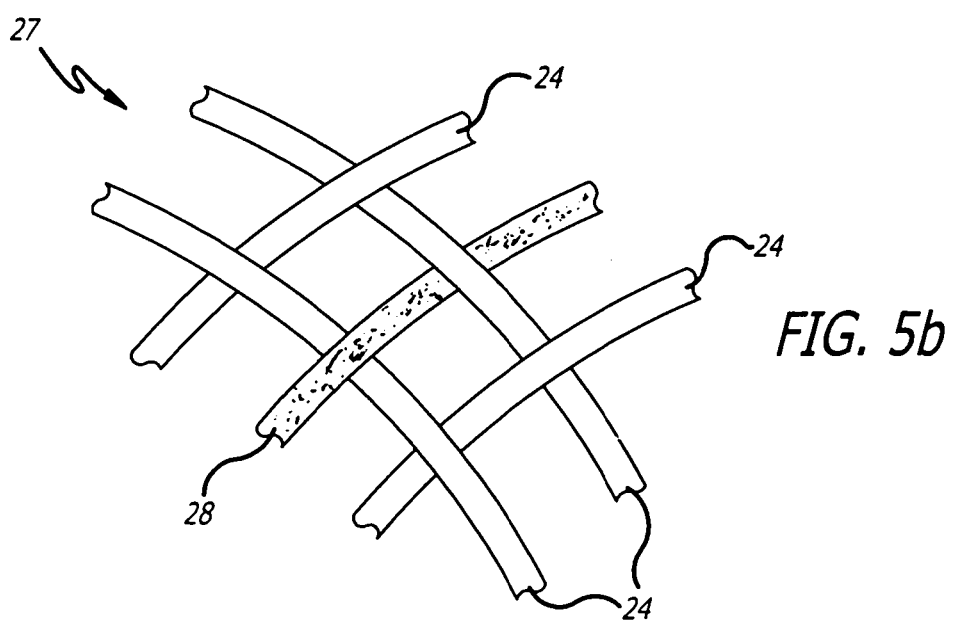
FIG. 5b shows a perspective view of an embodiment of an aneurysm treatment device comprising a structure having reactive material interwoven therein in a non-reacted state.
Figure 5C:
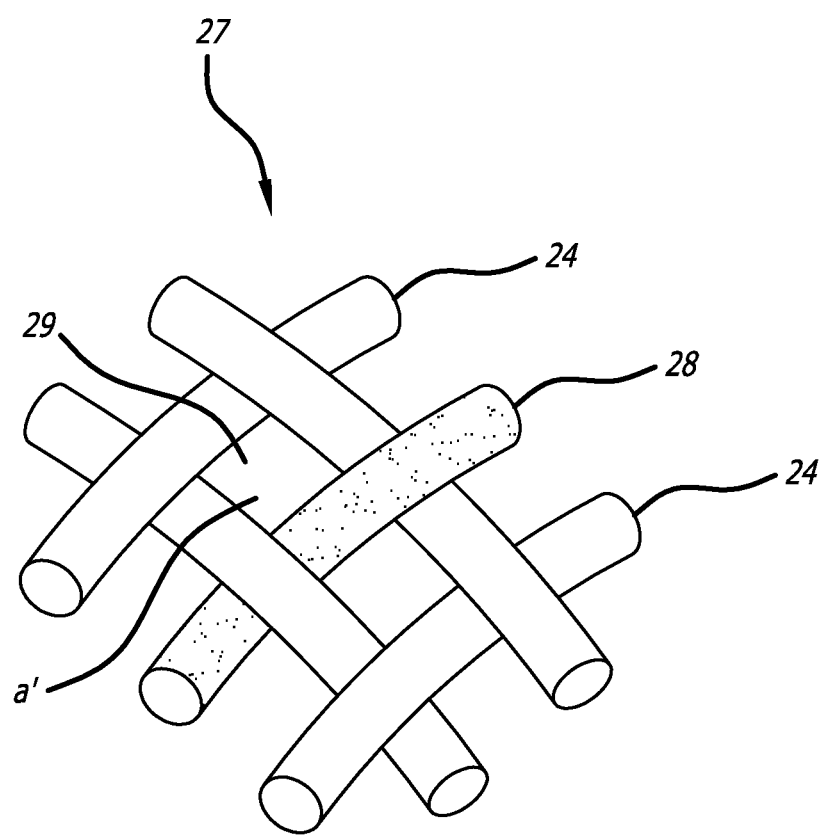
FIG. 5c shows a perspective view of an embodiment of an aneurysm treatment device comprising a structure having reactive material interwoven therein in a reacted state.

FIGS. 5b and 5c show an alternate embodiment of an aneurysm treatment device comprising a reactive material strand or wrap positioned on a support member 24. A number of support members 24 are interwoven thereby forming an interwoven structure 27. Reactive material or strands 28 may applied to a support member 24 or positioned within the interwoven structure 27 in a radial, axial, or radially and axial orientation. For example, a support member 24 may be wrapped with a reactive material strand 28. In an alternate embodiment, a reactive strand 28 may be disposed within the interwoven structure 27. Optionally, a reactive strand 28 may be interwoven within the structure 27. FIG. 5b shows an embodiment of the aneurysm treatment device with the reactive material 28 in a non-reacted state. As shown in FIG. 5b, the orifices 29 formed by the reactive material strand 28 and surrounding support members 24 have a first area of A. FIG. 5c shows the material strands 28 of the aneurysm treatment device in a reacted state wherein the orifices 29 formed by the reactive material strand 28 and surrounding support members 24 have a second area of A'. As shown, the second area A' of the orifices 29 in a reacted state is less than the first area A of the orifices in a non-reacted state, thereby limiting the flow therethrough. For example, the second area A' of the orifices 29 in a reacted state is at least about 20% less than the first area A of the orifices in a non-reacted state.

Referring again to FIGS. 4 and 5a, the support members 24 of the various embodiment of the aneurysm treatment device may be manufactured from a plurality of biologically-compatible materials. For example, in one embodiment at least one support member 24 is manufactured from materials including, without limitation, platinum, gold, tantalum, titanium, stainless steel, tungsten, Nitinol, shape memory alloys, formed reactive material, or other suitable material. Optionally, at least one support member 24 may be manufactured from a variety of biologically-compatible polymer materials, including, but not limited to, polyurethane, polyvinyl alcohol, polyester, polytetrafluoroethylene, silicone, acrylic, or similar polymeric materials. At least one support member 24 may incorporate radio-opaque or echogenic materials or agents, thereby enabling the surgeon to precisely position the device within an aneurysm, blood vessel, or other hollow organ.

At least one support member 24 used in forming an aneurysm treatment device includes at least one reactive material 28 applied thereto. The reactive material 28 may be applied in a variety of ways known in the art. For example, one or more support members 24 may be coated with a reactive material 28. In an alternate embodiment, one or more support members 24 may have a reactive material 28 selectively applied thereto. For example, a reactive material 28 may be wrapped around or adhesively bonded to a portion of a support member 24. FIGS. 5d-5e show various embodiments of an aneurysm treatment device having a reactive fiber strand 28 applied thereto. As shown, the aneurysm treatment device comprises a support member 24 defining an internal passage 25. A portion of the support member 24 includes a reactive fiber stand 28 encircling a portion of the support member 24. In one embodiment, the reactive fiber strand may be adhesively coupled to the support member 24. For example, a fiber substrate having an adhesive applied to one surface and a reactive material 28 applied thereto may be positioned on or selectively applied to one or more support members 24.

The support member 24 receiving the reactive material strand 28 may have a constant or variable diameter or tangential width. For example, FIGS. 5f and 5g show an embodiment of a support member 24' having a variable tangential width. As such, the diameter of the support member 24' having the reactive material wrap 28 applied thereto is approximately equal to the diameter of surrounding support members 24. As a result, the diameter of the aneurysm treatment device in a non-reacted state remains substantially constant. In one embodiment, the reactive material wrap 28 is closely wound about the support member 24'. In an alternate embodiment, the reactive material wrap 28 may be intermittently applied to the support member 24'.

Optionally, at least one support member 24 and\or the reactive material 28 applied to the support member 24 may include one or more therapeutic agents applied thereto. Exemplary therapeutic agents include, for example, embolizing factors, anti-embolizing factors, and anti-restenotic compounds. For example, the reactive material 28 applied to one or more support members 24 may be chemically doped or impregnated with a drug, compound, and/or endothelial cell assays to promote endothelial cellular adhesion. An exemplary coating is described in US Patent Application Publication Number 2002/0049495 to Kutryk et al. which is incorporated in its entirety by this reference. In an alternate embodiment, the reactive material 28 applied to one or more support members 24 may be chemically doped or impregnated with a drug or compound to promote tissue growth or impart other therapeutic benefit about the support member 24.

The reactive material 28 may be fabricated from a plurality of materials capable of expanding or volumetrically changing over time within the presence of blood or other fluid. For example, the Applicant's co-pending U.S. patent application Ser. No. 09/804,935 filed on Mar. 13, 2001 entitled "Hydrogels That Undergo Volumetric Expansion In Response To Changes In Their Environment And Their Methods Of Manufacture And Use" discloses a hydrogel useful as a reactive coating or material 28 for treating aneurysms. The above-referenced hydrogel comprises 1.25 g (0.021 moles) acrylamide, 0.87 g (0.009 moles) sodium acrylate, 0.005 g (0.00003 moles) N,N-methylenebisacrylamide, 7.95 g water, and 4.5 g sodium chloride (<10 micron particle size) added to an amber jar. The initiators, 53 microliters of N,N,N',N-tetramethylethylenediamine and 65 microliters of 20% w/w ammonium persulfate in water, are added and the solution is aspirated into a 3-cc syringe. The solution is then injected into 0.025" ID tubing and allowed to polymerize for 2 hours. The tubing is cut into 2-inch sections and dried in a vacuum oven. The dried hydrogel is washed 3 times in distilled water for 10-12 hours, 2 hours, and two hours, respectively, to remove porosigen, any unreacted monomer and any unincorporated monomers. The hydrogel may then be cut into sections of approximately 0.100 inch length called "pellets" and skewered with a platinum coil/wire assembly. In the alternative, the hydrogel may be drawn or formed into fibrous strands or portions of similar size and dimension as the support members 24. These pellets or strands are then hydrated in alcohol and dried under vacuum at approximately 55 C for about 2 hours.

Thereafter, the dried pellets or strands are then placed in 50% hydrochloric acid/50% water and incubated for about 70 hours at 37 C. After the incubation, the excess hydrochloric acid solution is rinsed off of the pellets or strands with consecutive rinses of a) 70% isopropyl alcohol: 30% water for about 5 minutes, b) 100% isopropyl alcohol for about 15 minutes, c) 100% isopropyl for about 15 minutes and d) 100% isopropyl alcohol for about 15 minutes. The hydrogel pellets or strands are then dried under vacuum at 55 C for at least 2 hours. Prior to or following the complete drying process, the pellets or strands may be selectively applied to the at least one support member 24 as desired in a plurality of ways. In one embodiment the reactive material 28 is applied to the entire surface of a support member 24. For example, the reactive material 28 may be maintained in a liquid form and a support member 24 may be submerged therein, thereby coating the entire surface of the support member 24. In an alternate embodiment, the reactive material 28 is selectively applied to a portion of the support member 24. For example, the reactive material 28 may be selectively applied to the portion of a support member 24 which will engage a wall of a blood vessel. Optionally, a strand of the reactive material 28 may be wound about or around a support member 24. In another embodiment, the reactive material 28 may be applied to a substrate having a biologically compatible adhesive applied thereto. Thereafter, the substrate may be adhered to a support member 24 thereby applying the reactive material 28 thereto.

Once implanted in vivo, the reactive material 28 of the present embodiment becomes fully swollen after approximately one hour at physiological pH (about 7.4). For example, in one embodiment the reactive material 28 positioned on the support member 24 from a diameter of about 0.026 inch to a diameter of about 0.035 inch. As such, the cross sectional diameter of the support member 24 having reacted reactive material 28 thereon is about 25% larger than the cross sectional diameter of the support member 24 having non-reacted reactive material 28 thereon. Alternatively, the strands of reactive material 28 may be woven or integrated into the support structure. Optionally, the support structure 24 may be manufactured from a reactive material 28 without a substrate 26. (See FIG. 4)

FIGS. 6-9 show an embodiment of an aneurysm treatment device useful in isolating an aneurysm from a blood vessel. As shown in FIG. 6, the aneurysm treatment device comprises a vascular patch device 30 having a body member 32 formed by a plurality of interwoven or otherwise joined support members 24 axially displaced in relation to each other and capable of supporting weakened vascular tissue. The interwoven support members 24 form a plurality of fenestrations 34. In FIGS. 6-8, a reactive material 35 is selectively applied to the interwoven support members 24. As illustrated, the present embodiment permits the isolation and embolization of an aneurysm formed on a blood vessel without substantially occluding blood flow therethrough. As shown in FIG. 7, the vascular patch device 30 is formed by the plurality of support members 24 and may have an arcuate profile 36. In one embodiment, the arcuate profile 36 may be selected to approximate the radius of curvature of the receiving blood vessel, thereby further limiting blood vessel occlusion following implantation. The vascular patch device 30 may be manufactured in a variety of sizes, lengths, and radiuses. For example, the vascular patch device 30 may approximate 270 degrees of the receiving blood vessel, thereby using mechanical force to secure the device within the blood vessel. If desired, the vascular patch device 30 may incorporate malleable support members 24, thereby permitting the surgeon to adjust the arcuate profile 36 to conform to the radius of curvature of the receiving blood vessel during implantation.

Referring to FIG. 8, a vascular patch device 30 is shown positioned within a blood vessel 14 proximate to an aneurysm 10, wherein the device 30 traverses the opening 38 to the aneurysm cavity 18 formed by the neck portion 12. As shown, the expansion of the reactive coating 35 results in a decrease in the size of the fenestrations 34 formed in the vascular patch device 30, thereby reducing the amount of blood entering the aneurysm. In an alternate embodiment, the device 30 may include a plurality of attachment devices (not shown) to assist in implanting and securing the device within a blood vessel. The attachment devices may include, for example, hooks, barbs, or similar devices manufactured from a plurality of materials, such as platinum, gold, tantalum, titanium, stainless steel, Nitinol, or other suitable material. In an alternate embodiment, the vascular patch device 30 may incorporate alternate attachment mechanisms, including, without limitation, adhesive materials, mechanical attachment mechanisms, or vacuum attachment mechanisms. FIG. 9 shows a cross sectional view of a blood vessel 14 having the vascular patch device 30 positioned proximate to an aneurysm 10. Those skilled in the will appreciate the present embodiment may be manufactured in a plurality of sizes, thereby enabling usage in various blood vessels to repair a plurality of aneurysms.

FIGS. 10-12 show an alternate embodiment of an aneurysm treatment device useful in treating aneurysms. As shown in FIG. 10, the aneurysm treatment device includes a resilient coiled bridge device 40 having a sinusoidal body member 42 defining a plurality of openings 44. The body member 42 may be formed along an arc 46, thereby aiding in the implantation of the device while limiting the occlusion of blood vessel. The resilient body member 42 may be compressed along the line 48 to enable delivery and positioning of the coiled bridge device 40 in vivo. Upon placement of the coiled bridge device 40 the resiliency of body member 42 exerts an outward pressure along line 50, wherein the resilient body member 42 engages the blood vessel wall (not shown). In an alternate embodiment, the coiled bridge device 40 may be used to provide mechanical support to weakened vascular tissue. As shown in FIG. 10, the body member 42 is coated with or otherwise disposes a reactive coating, thereby occluding or otherwise inhibiting the flow of blood to the aneurysm. FIG. 11 shows an alternate embodiment of the coiled bridge device 40 comprising a resilient sinusoidal body member 42 having at least one reactive section 52 disposed thereon, and defining a plurality of openings 44. The reactive portions 52 are areas selectively coated or otherwise incorporating a reactive material as defined above. The present embodiment permits the embolization of the aneurysm while limiting the occlusion within the blood vessel. FIG. 12 shows a cross sectional view of an aneurysm treatment device positioned within a blood vessel 14 wherein the at least one reactive section 52 occludes or inhibits blood flow to an aneurysm 10.

FIGS. 13-15 show yet another embodiment of an aneurysm treatment device useful in treating aneurysms formed on weakened vascular tissue. FIGS. 13-15 show various implantable expandable intraluminal prosthetic devices commonly referred to as "stents" capable of embolizing or isolating an aneurysm formed on weakened blood vessel tissue. In an alternate embodiment, the intraluminal vascular prosthetic devices may be used to provide mechanical support to weakened vascular tissue. As shown in FIG. 13, a helical expandable stent 54 comprises a cylindrical body member 60 disposed between a first end 56 and a second end 58. The cylindrical body member 60 defines a central lumen 62 co-axially aligned with the longitudinal axis 64 of the stent 54. The helical expandable stent 54 has a first diameter, D, thereby enabling insertion and positioning of the device within a blood vessel, and a larger second diameter, D', which is capable of engaging and supporting a blood vessel wall. As shown, a reactive material 66 is selectively applied to the external surface of the helical expandable stent 54. FIG. 14 shows an alternate embodiment of the helical expandable stent 54, comprising a cylindrical body member 60 having a first end 56 and a second end 58. The cylindrical body member 60 further comprises at least one reactive section 66 disposed thereon, thereby enabling the embolization or isolation of an aneurysm while limiting blood vessel occlusion. FIG. 15 shows cross sectional view of the present embodiment positioned within a blood vessel 14, wherein the at least one reactive section 66 occludes or otherwise inhibits blood flow to an aneurysm 10.

Figure 18:
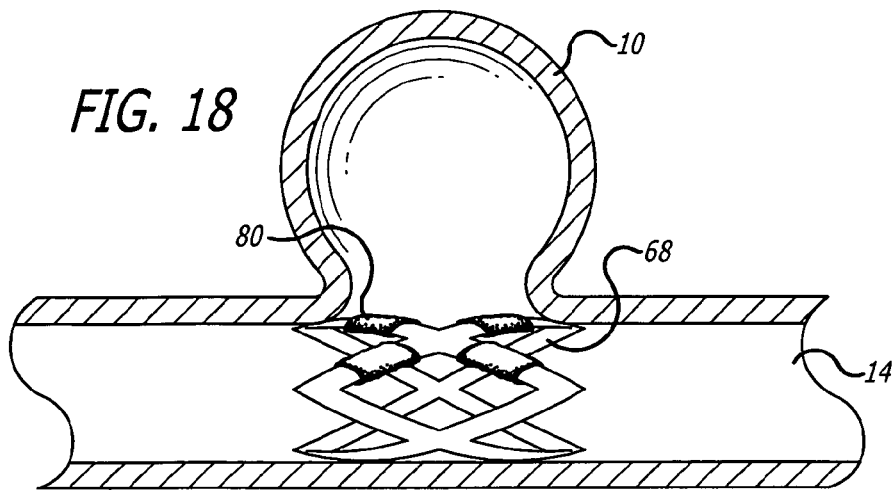
FIG. 18 shows a cross-sectional view of an embodiment of an aneurysm treatment device comprising a reticulated support device positioned within a blood vessel proximate a vascular aneurysm.

In another embodiment, FIGS. 16-18 show various embodiments of reticulated expandable intraluminal stents. As shown in FIGS. 16 and 17, the reticulated stent 68 comprises a first end 70 and a second end 72, having a cylindrical reticulated body 74 positioned therebetween. The cylindrical reticulated body 74, which is comprised of a series of interconnected support members 24, defines a flow lumen 76 co-axially aligned along the longitudinal axis 78 of the stent 68 having a first compacted diameter D, and a second larger diameter D'. As shown in FIGS. 16-18, a reactive material may be applied to the external portion of the stent 68. Alternatively, the reactive material may be applied to selected areas or individual support members 24 may be manufactured from reactive material or otherwise incorporated therein. FIG. 18 shows an embodiment of the reticulated expandable stent 68 positioned within a blood vessel 14, wherein a reactive section 80 is occluding or otherwise inhibiting the flow of blood to an aneurysm 10.

Figure 19:
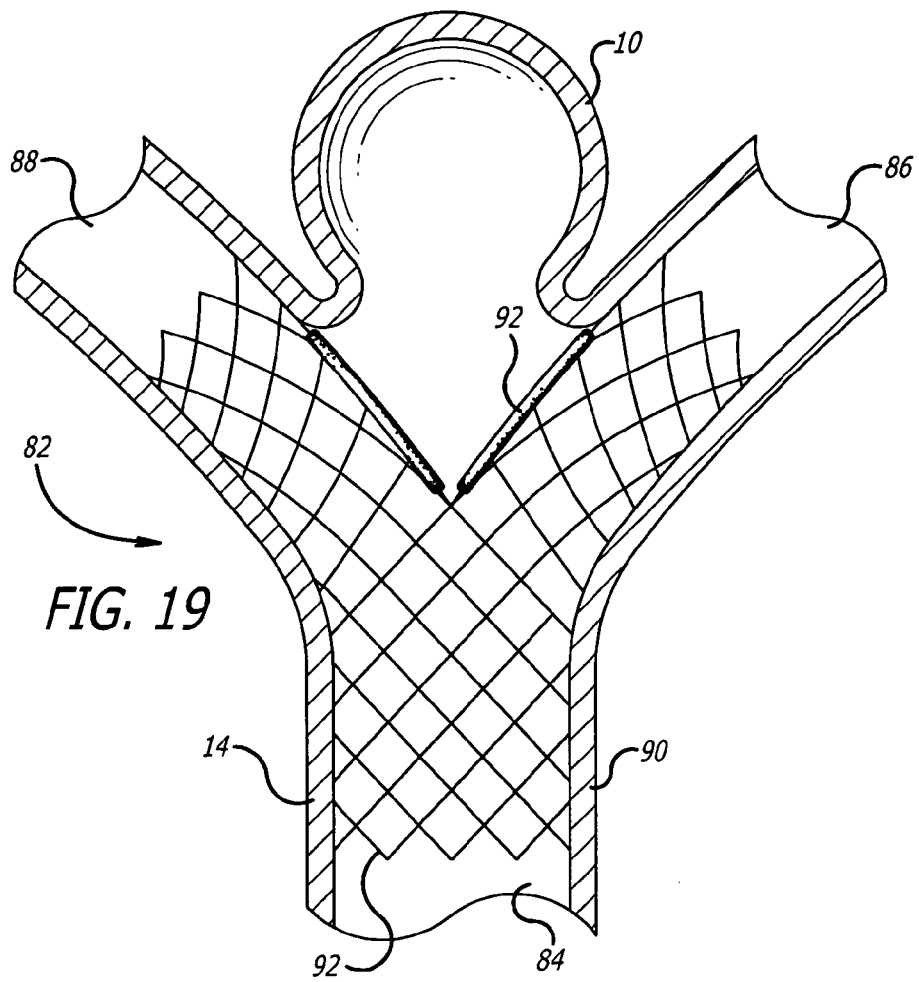
FIG. 19 shows a cross-sectional view of an embodiment of an aneurysm treatment device comprising a bifurcated stent device positioned within a blood vessel proximate to a vascular aneurysm.

FIG. 19 shows an embodiment of an occlusive bifurcated supports. As shown in FIG. 19, the occlusive bifurcated support 82 comprising a first end 84, a second end 86, and a third end 88 and having a cylindrical body 90 positioned between the first, second, and third ends, 84, 86, and 88, respectively. The cylindrical body 90 further defines an internal lumen 92, which is in communication with the first, second, and third ends, 84, 86, and 88, respectively. The occlusive bifurcated support 82 has first diameter D, thereby enabling insertion and positioning of the device within a blood vessel, and a larger second diameter D', which is capable of engaging a blood vessel wall. As such, the cylindrical body 90 may be manufactured from a plurality of interlocking or otherwise joined support members 24, and may be reticulated. Reactive material 92 is incorporated into the cylindrical body 82, thereby occluding the aneurysm 10 formed on the blood vessel 14.

FIGS. 20 and 21 show an embodiment of an occlusive support device. As shown in FIG. 20, an aneurysm 110 may form on a blood vessel 114 at a vascular junction. The blood vessel 114 includes a first passage 116, a second passage 118, and a third passage 120. The occlusive support device 100 comprises one or more support members 122 forming a first end 124 and a second end 126 and defining a lumen 128 therethrough. One or more fenestrations 130 may be defined by the one or more support members 122. When implanted the one or more support member 122 provide support along line L to the surrounding tissue while permitting blood to flow through the fenestrations 130 formed by the support members 122. An end cap may be secured to the second end 126 of the occlusive support device 100. In one embodiment the end cap 132 is comprised of a support member 122 having reactive material 133 applied thereto. For example, as shown in FIGS. 20 and 21 the end cap 132 comprises a support member 122 formed in a circular shape of decreasing diameter. In an alternate embodiment, the end cap 132 may be comprised of a plurality of interwoven support members 122 thereby forming a fenestrated end cap. The end cap 132 may be comprised from one or more filamentary elements that can easily be linearized for movement through a catheter. Optionally, the end cap 132 is comprised of reactive material 133. As such, the end cap 132 may have no reactive material thereon, reactive material 133 applied thereto, or manufactured solely from one or more reactive materials 133. Once implanted, the end cap 132 decreases the flow of blood from the first passage 116 of the blood vessel into aneurysm 110 formed at the vascular junction, thereby directing the blood flow into the second and third passages 118, 120. As shown in FIG. 21, a space-occupying material 136 may be injected into the aneurysmal space 138 formed in the aneurysm 110. For example, a catheter 134 may be advanced though occlusive device 100 positioned within a blood vessel 114 and inserted through the end cap 132 into the aneurysmal space 138. Thereafter, a space occupying material 136 may be injecting or inserted into the aneurysmal space 138 from the catheter 134. Exemplary space occupying material 136 include, without limitation, hydrogels, hog hair, microfibrillar collagen, various polymeric agents, material suspensions, metallic or radio-opaque materials, and other space filling materials. In an alternate embodiment, therapeutic agents may be delivered to the aneurysmal space 138 through the catheter 134. Once the space occupying material 136 has been inserted into the aneurysmal space 138 the end cap 132 may be used to maintain the space occupying material 136 within the aneurysm 110 or to facilitate the formation of a substantially continuous surface bridging the neck of the aneurysm 110.

Figure 22:
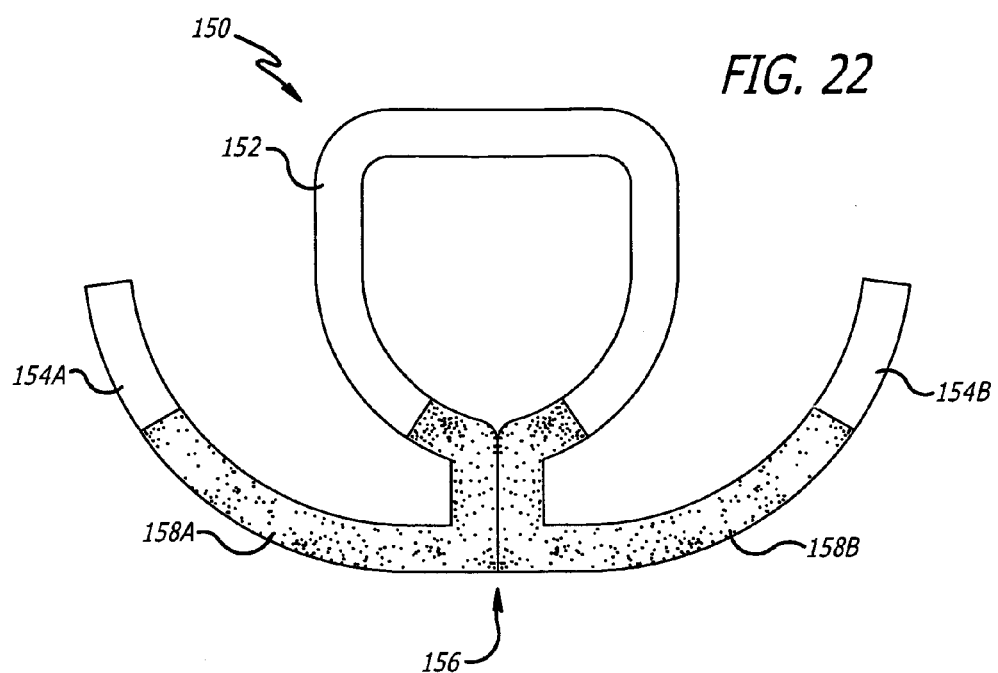
FIG. 22 shows a perspective view of an embodiment of an aneurysm treatment device comprising an intra-aneurysmal bridge device an aneurysm treatment device useful in restricting the flow of blood to a vascular aneurysm.
Figure 23:
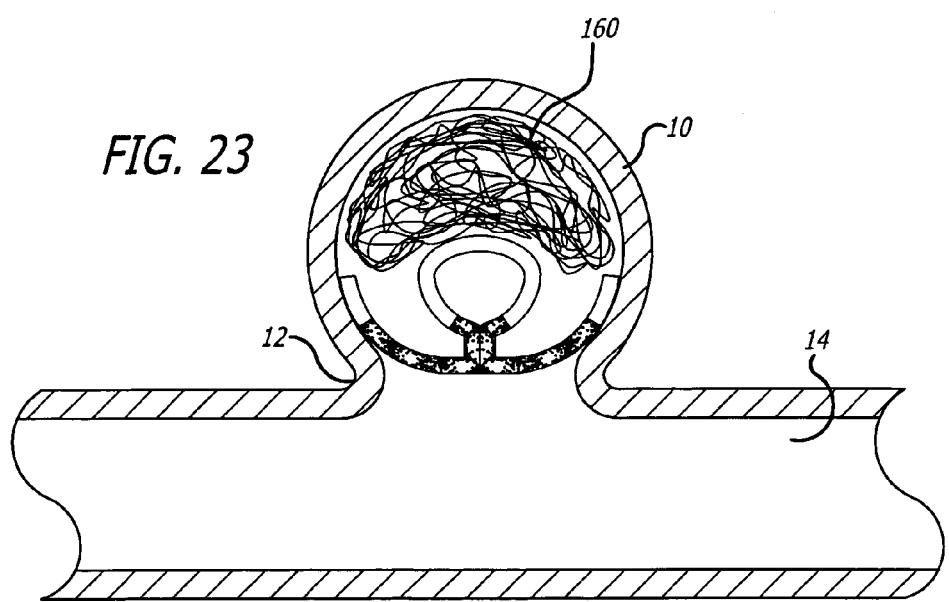
FIG. 23 shows a sectional view of an embodiment of the aneurysm treatment device shown in FIG. 22 positioned within a vascular aneurysm.

FIGS. 22 and 23 show an embodiment of an intra-aneurysmal neck bridge structure. As shown, the intra-aneurysmal neck bridge structure 150 comprises device body 152 in communication with at least two engagement members 154A and 154B cooperatively forming a device joint 156. In one embodiment, the device joint 156 sealably isolates the aneurysm from the flow of blood through the blood vessel. The engagement members 154A-B are formed to approximate the radius of curvature of the aneurysm thereby providing an interface between the device and the aneurysm. Reactive portions 158A-B are positioned on the engagement members 154A-B, respectively. As shown in FIG. 23, a reactive or occlusive material 160 may be inserted into the aneurysm 162 prior to or after applying the intra-aneurysmal neck bridge structure 150. Such reactive or occlusive materials 160 may include, for example, a plurality of materials such as hydrogels, hog hair, microfibrillar collagen, various polymeric agents, material suspensions, metallic or radio-opaque materials, and other space filling materials.

The present application further discloses methods of treating vascular aneurysms. In the one embodiment, a method of percutaneously inserting an aneurysmal treatment device into an aneurysm is disclosed and includes percutaneously inserting am aneurysmal treatment device into a blood vessel, advancing the treatment device to a location proximate to a vascular aneurysm, and applying the device to the aneurysm or surrounding tissue without substantially restricting blood flow through the blood vessel. The aneurysm treatment devices disclosed in the present application may be delivered to a situs in vivo in a plurality of manners, including, for example, on guidewires, balloon catheters or through micro-catheters. FIG. 24 shows an exemplary embodiment 170 of an aneurysm treatment device being applied to an aneurysm 172 using a balloon micro-catheter 174.

In practice, the surgeon positions an aneurysm treatment device, for example, an expandable reticulated stent 170 on a delivery device, for example, a micro-balloon catheter 174. Thereafter, a first incision is made proximate a blood vessel and a guidewire 176 is inserted therein. Commonly, the guidewire will enter the circulatory system through the femoral artery, the femoral vein, the jugular vein, the carotid artery, or a similar blood vessel. The guidewire 176 may then be directed through the circulatory system to a location proximate to the aneurysm 172 and, thereafter, made to exit the body through a remote exit point. The delivery device 174 and stent 170 may then be advanced along the guidewire 176 and positioned proximate to the aneurysm 172. Typically, visualization methods, such as fluoroscopy, ultrasound visualization, or echogenic location are utilized to precisely position the delivery device near or within the aneurysm 172. Once positioned, the micro-balloon 174 is inflated and the expandable reticulated stent 170 is applied to the tissue. The portion of the expandable reticulated stent 170 disposing the reactive material 178 is positioned proximate to the aneurysm. Thereafter, the delivery device 174 and guidewire 176 are removed from the body. The activation of the reactive material 178 selectively applied to the stent 170 restricts or occludes the flow of blood to the aneurysm 172. The activation process may result from a plurality of occurrences, including, for example, the presence of a physiological pH for an extended period, the presence of an enzyme or other material within the blood, electromagnetic-activation resulting from the introduction of a pre-determined wavelength of electromagnetic energy. The procedure above discloses one such activation method, however, other activation methods known in the art are contemplated.

In closing it is understood that the embodiments of the aneurysm treatment device disclosed herein are illustrative of the principles of the invention. Other modifications may be employed which are within the scope of the invention. Accordingly, the present invention is not limited to that precisely as shown and described in the present invention.

What is claimed is:

1. An apparatus for treating vascular aneurysms, comprising:
    a support member forming a stent that is radially expandable to a diameter of a blood vessel; and,
    a reactive fiber strand encircling a portion of said support member.

2. The apparatus of claim 1, wherein said reactive fiber strand comprises a reactive material having a reacted state that increases resistance to the flow of blood to an aneurysm.

3. The apparatus of claim 1, wherein said reactive fiber strand comprises a hydrogel that volumetrically expands over time within the presence of blood.

4. The apparatus of claim 1, wherein said reactive fiber strand is adhesively coupled to the support member.

5. The apparatus of claim 1, wherein said support member has a constant diameter.

6. The apparatus of claim 1, wherein said support member has a variable diameter.

7. The apparatus of claim 1, wherein said support member has a variable width.

8. The apparatus of claim 1, wherein said support member has a region of reduced width and wherein said reactive fiber strand is wrapped around said region of reduced width.

9. The apparatus of claim 8, wherein a width of said region of reduced width and said reactive fiber strand is substantially the same as a second portion of said support member adjacent to said region of reduced width.

10. The apparatus of claim 1, wherein a thickness of said portion of said support member and said reactive fiber strand is substantially the same as a second portion of said support member adjacent to said region of reduced width.

11. The apparatus of claim 1, wherein said reactive fiber strand is wound so as to form gaps between each of its windings.

12. The apparatus of claim 1, wherein said reactive fiber strand further comprises a core member of non-expansible material.

13. The apparatus of claim 1, wherein a reactive material of said reactive fiber strand comprises a compound to promote tissue growth.

14. The apparatus of claim 1, wherein said support member comprises a compound to promote tissue growth.

15. The apparatus of claim 1, wherein said support member forms a zig-zag shape.

16. The apparatus of claim 1, wherein said support member defines a shape having an internal passage.

17. The apparatus of claim 1, further comprising a plurality of support members, wherein said reactive fiber strand is selectively wrapped around each of said plurality of support members.

18. The apparatus of claim 1, wherein said reactive fiber strand has a thickness between about 10% and 200% of the largest thickness of said support member.

19. An apparatus for treating vascular aneurysms, comprising:
    a support member forming an aneurysm treatment stent that is sized for delivery within a blood vessel and expandable to a diameter of said blood vessel; and,
    a reactive fiber strand wound around at least a portion of said support member.

20. A method of creating a vascular treatment apparatus for aneurysms, comprising:
    providing a support member forming a stent sized for delivery within a human blood vessel and being expandable to a diameter of said human blood vessel;
    winding a reactive fiber strand around at least a portion of said support member.

21. The method of claim 20, wherein said winding said reactive fiber strand further comprises winding said reactive fiber strand around a reduced diameter region of said support member.

22. The method of claim 20, wherein said reactive fiber strand comprise a hydrogel that volumetrically expands over time within the presence of blood.

23. The method of claim 20, wherein said reactive fiber strand is adhesively coupled to said support member.

\* \* \* \* \*